United States Patent [19]

Sakuma et al.

[11] Patent Number: 5,661,148

[45] Date of Patent: Aug. 26, 1997

[54] PYRROLO[2,3-D]PYRIMIDINE DERIVATIVES, PROCESS FOR PRODUCING THE SAME AND PHARMACEUTICAL PREPARATION COMPRISING THE SAME AS ACTIVE INGREDIENT

[75] Inventors: Yasuji Sakuma, Hachioji; Masaichi Hasegawa, Hino; Kenichiro Kataoka, Hino; Kenji Hoshina, Hino; Noboru Yamazaki; Takashi Kadota, both of Hachioji; Hisao Yamaguchi, Hino, all of Japan

[73] Assignee: Teijin Limited, Osaka, Japan

[21] Appl. No.: 478,686

[22] Filed: Jun. 7, 1995

Related U.S. Application Data

[63] Continuation of Ser. No. 203,494, Feb. 28, 1994, abandoned, which is a continuation of Ser. No. 24,380, Mar. 1, 1993, abandoned, which is a continuation-in-part of Ser. No. 863,168, Apr. 3, 1992, abandoned, which is a continuation-in-part of Ser. No. 838,813, Mar. 18, 1992, abandoned.

[30] Foreign Application Priority Data

Sep. 19, 1989 [JP] Japan ............................ 1-242933
Sep. 19, 1989 [WO] WIPO ............................ PCT90/01200

[51] Int. Cl.⁶ ........................ A61K 31/305; C07D 487/04; C07D 239/48
[52] U.S. Cl. ........................ 514/218; 514/234.2; 514/258; 540/575; 544/61; 544/117; 544/280; 544/320
[58] Field of Search ........................ 540/575; 544/61, 544/117, 280; 514/218, 234.2, 258

[56] References Cited

U.S. PATENT DOCUMENTS

| 4,352,795 | 10/1982 | Cook | 536/24 |
| 4,459,604 | 7/1984 | Cook | 536/24 |
| 4,968,686 | 11/1990 | Townsend | 540/280 |

FOREIGN PATENT DOCUMENTS

| 85440A | 1/1981 | European Pat. Off. |
| 0286028 | 3/1988 | European Pat. Off. |
| 3628223 | 8/1985 | Germany |
| 63-275598 | 11/1988 | Japan |
| 2179656A | 3/1987 | United Kingdom |

OTHER PUBLICATIONS

Sakuma, Chem Abs 115, 49717w (1991).
English Abstract of Nippon Noyaku Gakkaishi, vol. 6, No. 9 (1981), Chem Abs 95, 163729v Jorgensen.
Chemica Scripta, vol. 28, pp. 201–204 (1988).
Derwent Abstract for DE 3628223 (1985).
Abstract for EP 57,548 (Derwent) 1981.
Derwent Abstract for FR 2574407 (1984).
Eiger Journal of Heterocyclic Chemistry, vol. 24, No. 2, pp. 425–430 (1987).
Ramasamy Journal of Heterocyclic Chemistry, vol. 25, No. 6, pp. 1893–1898 (1988).
Saxena Journal of Medicinal Chemistry, vol. 31, No. 8, pp. 1501–1506 (1988).
Derwent Abstract for DE 23628223 (1985).
Derwent Abstract for EP 57,548 (1981).
Derwent Abstract for EP 85, 440 (1981).

*Primary Examiner*—Mark L. Berch
*Attorney, Agent, or Firm*—Sughrue, Mion, Zinn, Macpeak & Seas

[57] ABSTRACT

A pyrrolo[2,3-d]pyrimidine derivative having the general formula [I]

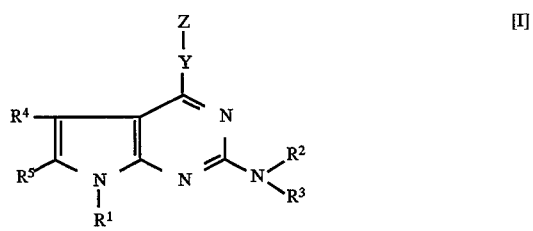

wherein $R^1$, $R^2$, $R^3$, $R^4$, $R^5$, Y and Z have the same definitions as those given in the description, a pharmaceutically acceptable acid addition salt thereof, and a pharmaceutical preparation comprising the same, are provided.

12 Claims, No Drawings

PYRROLO[2,3-D]PYRIMIDINE DERIVATIVES, PROCESS FOR PRODUCING THE SAME AND PHARMACEUTICAL PREPARATION COMPRISING THE SAME AS ACTIVE INGREDIENT

This is a continuation of application No. 08/203,494 filed on Feb. 28, 1994, abandoned which is a continuation of application Ser. No. 08/024,380, filed on Mar. 1, 1993, now abandoned, which is a continuation-in-part of application Ser. No. 07/863,168, filed Apr. 3, 1992, now abandoned, which is a continuation-in-part of application Ser. No. 07/838,813, filed Mar. 18, 1992, now abandoned.

TECHNICAL FIELD

The present invention relates to a novel pyrrolo[2,3-d]pyrimidine derivative, a process for producing same, and a pharmaceutical preparation comprising the derivative, and more particularly, relates to a novel pyrrolo[2,3-d]pyrimidine derivative having independently a substituted or unsubstituted amino group at the 2- and 4- positions of the pyrimidine ring, a pharmaceutically acceptable acid addition salt thereof, a process for producing same, and a pharmaceutical preparation comprising same as an active ingredient; particularly, a pharmaceutical preparation useful for the treatment, i.e., prophylaxis and therapy, of hypoxemia associated with respiratory diseases.

BACKGROUND ART

Compounds having the pyrrolo[2,3-d]pyrimidine skeleton of the formula:

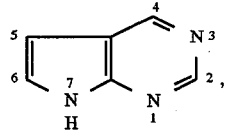

are known to have various important pharmacological actions. For example, it is known that antibacterial compounds are substituted by amino groups at both the 2- and 4- positions of the skeleton (see, U.K. Patent 812, 366, and Townsend L. B. et al, *J. Med. Chem.*, Vol. 31, 1501(1988), etc.). and that compounds useful as a herbicide and antibiotic have a primary amino group as the amino group (Okuda et al, *Nippon Noyaku-gakkaishi*, Vol. 6, 9(1981), Pedersen E. B. et al., *Chemica Scripta*, Vol. 28, 201(1988), etc.), other known antiviral compounds have an amino group at the 2- and 4- positions as well as a sugar residue at the 7- position of the skeleton (e.g., E.P. Publication No. 57548).

Nevertheless, in particular, pyrrolo[2,3-d]pyrimidine derivatives having an alkyl or alkenyl group at the 7-position, an amino group substituted by alkyl or alkenyl group at the 2- position, and a cyclic amino or chain substituted amino group at the 4- position, have not been described in the prior art.

DISCLOSURE OF INVENTION

The present inventors made extensive and intensive research into pyrrolo[2,3-d]pyrimidine derivatives and a process for producing same, and as a result, surprisingly found that, of the compounds not disclosed in the prior art, those of the formula I described below are particularly, efficacious for the prophylaxis and therapy of hypoxemia associated with respiratory diseases. Note, in the treatment of hypoxemia, to this day it has not been known that a compound can suffice in the light of both the pharmaceutical effect and toxicity there.

Thus, in accordance with the present invention there are provided, pyrrolo[2,3-d]pyrimidine derivatives having the formula I described below, pharmaceutically acceptable acid addition salts thereof, a process for producing same, as well as pharmaceutical preparations containing same derivatives or salts as an active ingredient:

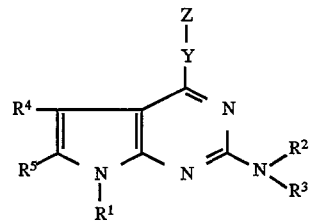

wherein $R^1$ represents a hydrogen atom, or an unsubstituted or substituted alkyl, alkenyl or arylalkyl group;

$R^2$ and $R^3$, independently of each other, represent a hydrogen atom, or an unsubstituted or substituted alkyl, alkenly, arylalkyl or alkylcarbonyl group; or $R^2$ and $R^3$ are optionally taken together with the adjacent nitrogen atom to form a mono-cyclic amino group;

$R^4$ and $R^5$ independently of each other, represent a hydrogen atom, halogen atom, or an unsubstituted or substituted alkyl group;

Y is a linking group bonded to the pyrimidine ring via a nitrogen atom therein of the formula

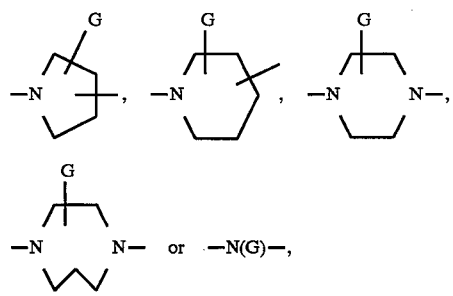

wherein G represents a hydrogen atom or an alkyl group;

Z represents a group bonded to a carbon or nitrogen atom in the linking group, and is a hydrogen atom, an unsubstituted or substituted alkyl, alkenyl, aryl, heteroaryl, arylalkyl, heteroarylalkyl, alkylcarbonyl, arylcarbonyl heteroarylcarbonyl, arylalkylcarbonyl, heteroarylalkylcarbonyl or heteroalicyclic group; or represents a group bonded to a carbon atom in the linking group, and is a carboxyl, hydroxyl; or an unsubstituted or substituted alkyloxycarbonyl, alkylcarbonyloxy, arylcarbonyloxy, arylalkylcarbonyloxy, heteroarylalkylcarbonyloxy, alkyloxy or alkyloxyiminoalkyl group; or mono- or di-alkylamino, mono- or di-alkylcarbonylamino, or N-alkyl-N-alkylcarbonylamino group; or Y and Z are taken together. to form morpholino or thio-morpholino group;

each substituent in said substituted group is substituted at a chain or cyclic moiety of the alkyl, alkenyl, aryalkyl, heteroarylalkyl, aryl, heteroaryl, or heteroalicyclic moiety, respectively, and represents an unsubstituted or substituted alkyl, alkyloxy, aryloxy, alkylcarbonyl, alkylcarbonyloxy, heteroalicyclic, hydroxy, mono- or di-alkylamino, amino, nitro, cyano group, or a halogen atom, wherein the substituted group, at a chain or cyclic moiety thereof, has further one or more substituents including alkyloxy, hydroxy, amino, nitro, cyano group and halogen atom, e.g., F, Cl, Br or I;

with a proviso that $R^2$ and $R^3$ do not represent a hydrogen atom at the same time, and that, when $R^1$ represents hydrogen atom, the combinations wherein one of $R^2$ and $R^3$ represents a hydrogen atom and another represents an alkyl group are excluded.

BEST MODE OF CARRYING OUT THE INVENTION

This invention is disclosed in detail below.

An alkyl moiety of each group, unless defined otherwise, is herein intended to mean a $C_1$–$C_{10}$ straight or branched chain aliphatic hydrocarbon residue, alicyclic hydrocarbon residue or chainaliphatic-alicyclic hydrocarbon residue, and is for example, methyl, ethyl, propyl, isopropyl, butyl, isobutyl, sec-butyl, tert-butyl, pentyl, hexyl, cyclopropyl, cyclobutyl, cyclopentyl, cyclohexyl, cyclopropyl-methyl and cyclobuthymethyl; preferably a $C_1$–$C_6$ lower alkyl group.

The term "alkenyl group" is intended to mean a $C_2$–$C_6$ straight or branched chain aliphatic hydrocarbon residue containing one double bond, for example, allyl, 1-methylallyl, 2-methylallyl, 2-butenyl, 2-methyl-2-butenyl, 3-methyl-2-buteny, 3-butenyl, 2-pentenyl, 3-methyl-2-pentenyl, 2-hexenyl, 3-cyclopropylally, 3-cyclopentenyl and 3-cyclohexenyl.

The term "aryl group" is intended to mean $C_6$–$C_{10}$ aromatic hydrocarbon cyclic groups constructed of a monoring or fused ring and examples thereof include phenyl, 1-naphthyl and 2-naphthyl. The term "heteroaryl group" is intended to mean 4- to 6-member of unsaturated cyclic groups containing 1 to 3 hetero atoms, e.g., N, S, O, which are constructed by a mono-cyclic ring or fused cyclic ring. Examples of the former include pyrrolyl, furyl, thienyl and pyridyl, and those of the latter include indolyl, benzofuryl, benzothienyl, pyrrolopirimidinyl and carbazolyl.

The term "arylalkyl group", which is constructed of said lower alkyl group and said aryl group, and containing in total 6 to 20 carbon atoms, for example, benzyl, 1-phenylethyl, 1-methyl-1-phenylethyl, 2-phenylethyl, 3-phenylpropyl, cinnamyl, diphenylmethyl (benzhydryl), triphenylmethyl, 1-naphthylmethyl, 1-(1-naphthy)ethyl, 1,2,3,4-tetrahydronaphtharen-1-yl.

The term "heteroarylalkyl group", which is constructed of said lower alkyl group and heteroaryl group, for example, is 2-pyrrolylmethyl, 2-furfuryl, 2-thienylmethyl, 2-pyridylmethyl, 2-(2-pyrrolyl)ethyl, 2-(2-furyl)ethyl and 3-(2-furyl)propyl.

The term "heteroalicyclic group" is intended to mean 4- to 6-member of saturated hetero mono-cyclic groups containing 1 to 3 hetero atoms, e.g., N, S, O, and, for example, pyrrolidinyl, tetrahydrofuryl, tetrahydrothiophen-yl, piperidinyl, morpholinyl, thiomorpholinyl and tetrahydropyranyl.

The above-described alkyl, alkenyl, aryl, heteroaryl, arylalkyl, heteroarylalkyl and heteroalicyclic groups may have a substituent in the chain moiety or cyclic moiety thereof, and examples of the substituent include an unsubstituted or substituted alkyl, alkyloxy, aryloxy, alkylcarbonyl, alkylcarbonyloxy, heteroalicyclic, hydroxy, mono- or di-alkylamino, amino, nitro, cyano group, or a halogen atom, wherein the substituted group, at a chain or cyclic moiety thereof, has further one or more substitutents including alkyloxy, hydroxy, amino, nitro, cyano group and halogen atom, e.g., F, Cl, Br or I; The groups defined below also may have the above-described substituents in the chain portion or cyclic portion thereof.

In the present invention, the term "alkylcarbonyl group", which is constructed of said lower alkyl and carbonyl group, is intended to mean $C_2$–$C_7$ lower alkylacyl, groups, such as acetyl, propanoyl, butanoyl, 2-methylpropanoyl, pentanoyl, 2-methylbutanoyl, 3-methylbutanoyl, pivaloyl, hexanoyl and cyclopropylcarbonyl.

The term "arylcarbonly group", which is constructed of said aryl and carbonyl group, is intended to mean, for example, benzoyl, toluoyl, naphthoyl.

The term "heteroarylcarbonyl group", which is constructed of said heteroaryl and carbonyl group, is intended to mean, for example, 2-pyrrolecarbonyl, 2-furancarbonyl and 2-thiophenecarbonyl.

The term "arylalkylcarbonyl group", which is constructed of said arylalkyl and carbonyl group, is intended to mean $C_7$–$C_{19}$ arylalkylcarbonyl groups, such as phenylacetyl, 3-phenylpropanoyl, 4-phenylbutanoyl, cinnamoyl, diphenylacetyl and naphthylacetyl.

The term "heteroarylalkylcarbonyl group", which is constructed of said heteroarylalkyl and carbonyl group, is intended to mean, for example, 2-pyrrolylacetyl, 2-furylacetyl and 2-thienylacetyl.

The term "alkyloxycarbonyl group", which is a carboxylic acid ester residue containing said alkyl group, is intended to mean $C_2$–$C_7$ lower alkyloxycarbonyl groups, such as methoxycarbonyl, ethoxycarbonyl, propoxycarbonyl, isopropyloxycarbonyl, butoxycarbonyl, tert-butyloxycarbonyl and cyclohexyloxycarbonyl.

The term "alkylcarbonyloxy group" which is constructed of said alkylcarbonyl and oxy group, is intended to mean $C_2$–$C_7$ lower alkylcarbonyloxy groups, such as acetoxy, propanoyloxy, butanoyloxy, 2-methylpropanoyloxy, pentanoyloxy, pivaloyloxy and hexanoyloxy.

The term "arylcarbonyloxy group", which is constructed of said arylcarbonyl and oxy group, is intended to mean, for example, benzoyloxy, toluoyloxy, naphthoyloxy.

The term "heteroarylcarbonyloxy group", which is constructed of said heteroarylcarbonyl and oxy group, is intended to mean, for example, 2-pyrrolecarbonyloxy, 2-furancarbonyloxy and 2-thiophenecarbonyloxy.

The term "arylalkylcarbonyloxy group", which is constructed of said arylalkylcarbonyl and oxy group, is intended to mean lower arylalkylacyloxy groups, such as phenylacetoxy, 3-phenylpropanoyloxy, 4-phenylbutanoyloxy and cinnamoyloxy.

The term "heteroarylalkylcarbonyloxy group", which is constructed of said heteroarylalkylcarbonyl and oxy group, is intended to mean, for example, 2-pyrrolylacetoxy, 2-furylacetoxy and 2-thienylacetoxy.

The term "alkyloxy group", which is constructed of said alkyl and oxy group, is intended to mean a $C_1$–$C_6$ lower alkyloxy group; such as methoxy, ethoxy, propoxy, butoxy, isopropyloxy, sec-butyloxy, tert-butyloxy, pentyloxy, cyclopropyloxy, cyclopropylmethyloxy, and cyclohexyloxy.

The term "alkyloxyiminoalkyl group" represents a group that, in the alkylcarbonyl groups, the oxygen atom is replaced with a group N-O-alkyl, and has the formula:

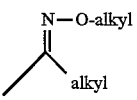

The term "mono- or di-alkylamino, mono- or di-alkylcarbonylamino or N-alkyl-N-alkylcarbonylamino group", represents amino groups substituted by one or two substituents selected from the same or different said lower alkyl or lower alkylcarbonyl group such as, methylamino, ethylamino, propylamino, butylamino, cyclohexylamino, dimethylamino, diethylamino, N-methylbuthylamino, acetylamino, propanoylamino, pivaloylamino, N-methylacetylamino and N-ethytacetylamino group.

The term "halogen atom" is intended to mean a fluorine atom, a chlorine atom, a bromine atom and an iodine atom.

According to the above-described definitions, the $R^1$ in the general formula I includes a hydrogen atom, or an unsubstituted or substituted alkyl group, alkenyl group, arylalkyl group and alkylcarbonyl group.

Suitable specific examples of the alkyl group include methyl, ethyl, propyl, isopropyl, butyl, cyclopropyl, cyclopropylmethyl, trifluoromethyl, methoxymethyl, methoxyethoxymethyl and aminoethyl. Suitable specific examples of the alkenyl group include allyl, 2-methylallyl, 2-butenyl, 3-methyl-2-butenyl, 2-fluoroallyl, 3-fluoroally, 2-(trifluoromethyl)allyl and 3-butenyl. Suitable specific examples of the arylalkyl group include benzyl, 4-fluorobenzyl, 4-chlorobenzyl, 3-(trifluoromethyl)benzyl, 4-methoxybenzyl, 2-phenylethyl, 2-[(2-trifluoromethyl) phenyl]ethyl, triphenylmethyl and (4-methoxyphenyl) diphenylmethyl. Suitable specific examples of the alkylcarbonyl group include acetyl, trifluoroacetyl, propanoyl, 2-methylpropanoyl and butanoyl.

The $R^2$ and $R^3$ in the general formula I are respectively identical with the $R^1$, and suitable examples thereof as well are identical with those of $R^1$. The $R^2$ and $R^3$ may be taken together with an adjacent nitrogen atom to form a cyclic amino group. The cyclic amino group is a saturated five- to seven-membered ring and may further have at least one cyclic hetero atom (for example, N, O or S) in its ring other than the above-described nitrogen. Suitable specific examples of the cyclic amino group include 1-pyrrolidinyl, piperidino, 1-piperazinyl, 4-[bis(4-fluorophenyl)methyl]-1-piperazinyl, morpholino, thiomorpholino and 1-perhydro[1, 4]diazepinyl.

The $R^4$ and $R^5$ in the general formula I each independently represent a hydrogen atom, a halogen atom or an substituted or substituted alkyl group. Suitable specific examples of the halogen atom include a fluorine atom, a chlorine atom and a bromine atom. Suitable examples of the alkyl group include methyl, ethyl and trifluoromethyl.

In the general formula I, the Y represents a linking group, which is bonded to the pyrimidine ring via a nitrogen atom therein, of the formula

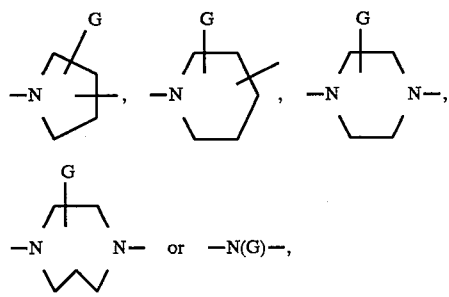

wherein G represents a hydrogen atom or an alkyl group. Suitable specific examples of the same include groups of the formula:

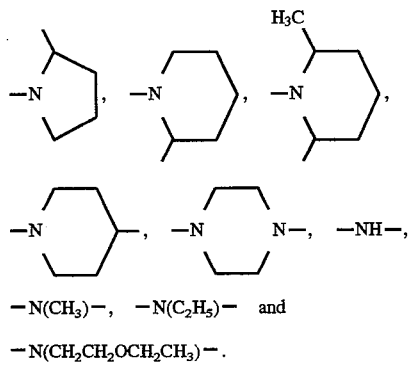

$-N(CH_3)-$, $-N(C_2H_5)-$ and $-N(CH_2CH_2OCH_2CH_3)-$.

In the general formula I, where Z bonds with a carbon atom or nitrogen atom in the linking group, suitable specific examples there of include a hydrogen atom; an alkyl group such as methyl, ethyl, propyl, isopropyl, tert-butyl, isobutyl, cyclohexyl, ethoxyethyl, 2-(3,5-dimethoxyphenoxy)ethyl, 1,3-dimethoxy-2-propyl, trans-4-hydroxycyclohexyl, trans -4-methoxycyclohexyl, cis-4-methoxycyclohexyl, trans-4-(2-ethoxy ethoxy)cyclohexyl, dimethyaminoethyl, morpholinoethyl, piperidinoethyl and tetrahydrofurfuryl; an alkenyl group such as allyl, 2-methylallyl, 2-butenyl, 3-methyl-2-butenyl, 2-fluoroally, 3-flouroallyl, 2-(trifluoromethyl)allyl and 3-butenyl; an arylalkyl group such as benzyl, 4-fluorobenzyl, 4-chlorobenzyl, 3-(trifluoromethyl)-benzyl, 4-methoxybenzyl, 1-phenylethyl, 1-methyl-1-phenylethyl, 2-phenylethyl, 2-(4-fluorophenyl)-ethyl, 2-(4-chlorophenyl)ethyl, 2-(4-methoxyphenyl)ethyl, 2-[2-(trifluoromethyl)phenyl]-ethyl, cinnamyl, diphenylmethy, bis(4-fluorophenyl)methyl, 1-(1-naphthyl)ethyl, 1,2,3,4-tetrahydronaphthalene-1-yl; a heteroarylalkyl group such as 2-pyrrolyl-methyl, 2-furfuryl, 2-thienylmethy and 3-(2-furyl)propyl; an aryl group such as phenyl, 4-fluorophenyl, 4-chlorophenyl and 4-methoxphenyl; an alkylcarbonyl group such as acetyl, trifluoroacetyl, propanoyl, 2-methylpropanoyl, butanoyl, pivaloyl, and cyclopropylcarbonyl; an arylcarbonyl group such as benzoyl, 4-fluorobenzoyl, 4-chlorobenzoyl, 3-methoxybenzoyl, 4-toluoyl and 1-naphthoyl; a heteroarylcarbonyl group such as 1-pyrrolocarbonyl, 2-furylcarbonyl and 2-thiophenecarbonyl; and an arylalkylcarbonyl group such as phenylacetyl, 4-fluorophenylacetyl, 3-phenylpropanonyl, cinnamoyl and diphenylacetyl; a heteroalicyclic group such as 2-pyrrolidnyl, 2-tetrahydrofuryl, piperidino, 4-piperidinyl, morpholino, 2-morpholinyl, 2-tetrahydropyranyl and 4-tetrahydropyranyl.

Where Z bonds with a carbon atom in the linking group, suitable other specific examples include a carboxyl group; hydoxyl group; alkyloxycarbonyl group such as methoxycarbonyl, ethoxycarbonyl, isopropoxycarbonyl and tert-butyloxycarbonyl; alkylcarbonyloxy group such as acetyloxy, propanoyloxy, 2-methylpropanoyloxy and pivaloyloxy; arylcarbonyloxy group such as benzoyloxy, 4-fluorobenzoyloxy, 4-toluoyloxy, 4-chlorobenzoyloxy, 4-methoxybenzoyloxy and 1-naphthoyloxy; arylalkylcarbonyloxy group such as phenylacetoxy, 4-fluorophenylacetoxy, 3-phenylpropanoyloxy, 4-phenylbutanoyloxy and cinnamoyloxy; alkyloxyl group such as methoxy, ethoxy, propoxy, isopropoxy and butoxy; and an alkyloxyiminoalkyl group such as groups of the formula:

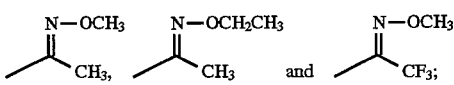

mono- or di-alkylamino, mono- or di-alkylcarbonylamino or N-alkyl-N-alkylcarbonylamino group such as methylamino, ethylamino, dimethylamino, diethylamino, acetylamino, pivaloylamino, N-methylacetylamino and N-ethylacetylamino.

Further, preferably Y and Z taken together represent a morpholino group and thiomorpholino group.

Suitable specific examples of pyrrolo[2,3-d]pyrimidine of the general formula I in accordance with the present invention include the compounds containing the substitUents described in the following table. Note, when the compound has asymmetric carbon atoms in structure thereof, the compounds of the present invention include all optical isomers.

TABLE

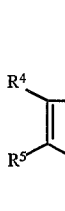

| Compound No. | R¹ | R² | R³ | R⁴ | R⁵ | Y | Z |
|---|---|---|---|---|---|---|---|
| 101 | H | H | 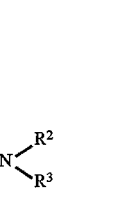 | H | H |  | F₂BH[1] |
| 102 | H | H | 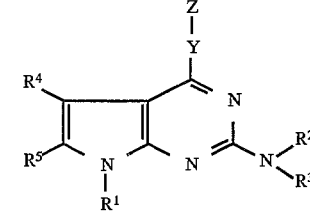 | CH₃ | CH₃ |  | F₂BH[1] |
| 103 | CH₃ | H | CH₃ | H | H | 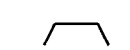 | F₂BH[1] |
| 104 | CH₃ | H |  | H | H |  | H |
| 105 | CH₃ | H | 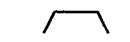 | H | H |  | 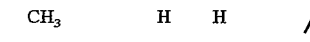 |
| 106 | CH₃ | H |  | H | H | 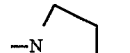 | CO₂H |
| 107 | CH₃ | H | 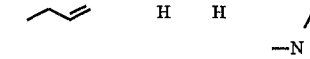 | H | H |  | H |
| 108 | CH₃ | H | 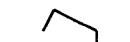 | Cl | H | 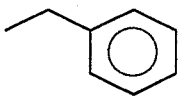 | H |
| 109 | CH₃ | H | 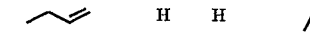 | H | H |  | 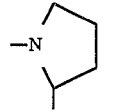 |

TABLE-continued

| Compound No. | R¹ | R² | R³ | R⁴ | R⁵ | Y | Z |
|---|---|---|---|---|---|---|---|
| 110 | CH₃ | H | ~= | H | H | -N-piperidyl | benzyl (CH₂-C₆H₅) |
| 111 | CH₃ | H | ~= | H | H | -N-piperidyl | F₂BH[1) |
| 112 | CH₃ | H | ~= | CH₃ | H | -N-piperidyl | F₂BH[1) |
| 113 | CH₃ | H | ~= | H | H | -N-piperidyl | C(=O)CH₃ |
| 114 | CH₃ | H | ~= | H | H | -N-piperidyl | C(=N-OCH₃)CH₃ |
| 115 | CH₃ | H | ~= | H | H | -N-piperidyl | CO₂H |
| 116 | CH₃ | H | ~= | H | H | -N-piperidyl | CO₂-iPr |
| 117 | CH₃ | H | ~= | H | H | -N-piperidyl | OH |
| 118 | CH₃ | H | ~= | H | H | -N-piperidyl | OCH₂CH₃ |
| 119 | CH₃ | H | ~= | H | H | -N-piperidyl | OAc |
| 120 | CH₃ | H | ~= | H | H | -N-piperidyl | O-C(=O)-C₆H₄-4-F |

TABLE-continued

| Compound No. | R¹ | R² | R³ | R⁴ | R⁵ | Y | Z |
|---|---|---|---|---|---|---|---|
| 121 | CH₃ | H | ⁓⫽ | H | H | -N(piperidine)- | NHCH₂CH₃ |
| 122 | CH₃ | H | ⁓⫽ | H | H | -N(piperidine)- | NH—Ac |
| 123 | CH₃ | H | ⁓⫽ | H | H | -N(piperidine)- | N(CH₃)₂ |
| 124 | CH₃ | H | ⁓⫽ | H | H |  | -N(morpholine)O |
| 125 | CH₃ | H | ⁓⫽ | H | H |  | -N(thiomorpholine)S |
| 126 | CH₃ | H | ⁓⫽ | H | H | -N(piperazine)N- | CH₃ |
| 127 | CH₃ | H | ⁓⫽ | CH₃ | CH₃ | -N(piperazine)N- | CH₃ |
| 128 | CH₃ | H | ⁓⫽ | H | H | -N(piperazine)N- | CH₂CH₃ |
| 129 | CH₃ | H | ⁓⫽ | H | H | -N(piperazine)N- | 4-F-C₆H₄ |
| 130 | CH₃ | H | ⁓⫽ | H | H | -N(piperazine)N- | CH₂C₆H₅ |
| 131 | CH₃ | H | ⁓⫽ | H | H | -N(piperazine)N- | 4-F-C₆H₄-CH₂ |
| 132 | CH₃ | H | ⁓⫽ | H | H | -N(piperazine)N- | 2-CH₃-C₆H₄-CH₂CH₂ |

TABLE-continued

| Compound No. | R¹ | R² | R³ | R⁴ | R⁵ | Y | Z |
|---|---|---|---|---|---|---|---|
| 133 | CH₃ | H | ∼ | H | H | −N⟨piperazine⟩N− | F₂BH[1] |
| 134 | CH₃ | H | ∼ | H | H | −N⟨homopiperazine⟩N− | F₂BH[1] |
| 135 | CH₃ | H | ∼ | H | H | −N⟨piperazine⟩N− | [2] |
| 136 | CH₃ | CH₃ | ∼ | H | H | −N⟨piperazine⟩N− | F₂BH[1] |
| 137 | CH₃ | ∼ | ∼ | H | H | −N⟨piperazine⟩N− | F₂BH[1] |
| 138 | CH₃ | Ac | ∼ | H | H | −N⟨piperidine⟩ | OAc |
| 139 | CH₃ | H | MMTr[3] | H | H | −N⟨piperazine⟩N− | −CH₂−C₆H₅ |
| 140 | ∼ | H | ∼ | H | H | −N⟨piperazine⟩N− | F₂BH[1] |
| 141 | ∼ | H | ∼ | H | H | −N⟨piperazine⟩N− | F₂BH[1] |
| 142 | ∼△ | H | ∼ | H | H | −N⟨piperazine⟩N− | F₂BH[1] |
| 143 | ∼ | H | ∼ | H | H | −N⟨piperazine⟩N− | F₂BH[1] |

TABLE-continued

| Compound No. | R¹ | R² | R³ | R⁴ | R⁵ | Y | Z |
|---|---|---|---|---|---|---|---|
| 144 | allyl | H | allyl | H | H | piperazine | -C(O)-CH=CH-C₆H₅ (cinnamoylmethyl ketone) |
| 145 | allyl | allyl | allyl | H | H | piperazine | F₂BH[1) |
| 146 | benzyl | H | allyl | H | H | piperazine | F₂BH[1) |
| 147 | 4-fluorobenzyl | morpholino | H | H | H | N-(CH₂CH₂)-N(C(O)CH₃)- | 4-chlorophenyl |
| 148 | CH₃ | H | cyclopropylmethyl | H | H | -NH- | α-methylbenzyl (isopropylphenyl) |
| 149 | CH₃ | H | allyl | H | H | -NH- | H |
| 150 | CH₃ | H | allyl | H | H | -NH- | cyclohexyl |
| 151 | CH₃ | H | allyl | H | H | -NH- | allyl |
| 152 | CH₃ | H | allyl | H | H | -NH- | -CH₂CH₂CH₂N(CH₃)₂ |
| 153 | CH₃ | H | allyl | H | H | -NH- | N-propylpiperidinyl |
| 154 | CH₃ | H | allyl | H | H | -NH- | -CH₂CH₂N(CH₂CH₂CH₃)₂ |
| 155 | CH₃ | H | allyl | H | H | -NH- | phenethyl |

TABLE-continued
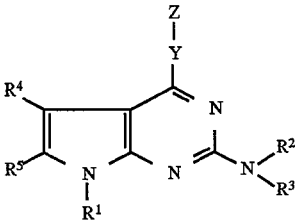
| Compound No. | R¹ | R² | R³ | R⁴ | R⁵ | Y | Z |
|---|---|---|---|---|---|---|---|
| 156 | CH₃ | H |  | H | H | —NH— | 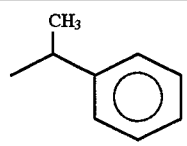 |
| 157 | CH₃ | H |  | H | H | —NH— | 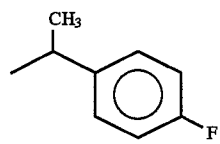 |
| 158 | CH₃ | H |  | H | H | —NH— | 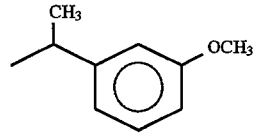 |
| 159 | CH₃ | H |  | CH₃ | CH₃ | —NH— | 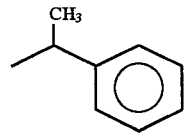 |
| 160 | CH₃ | H |  | H | H | —NH— | 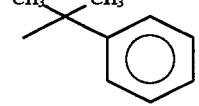 |
| 161 | CH₃ | H |  | H | H | —NH— | 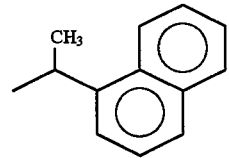 |
| 162 | CH₃ | H |  | H | H | —NH— | 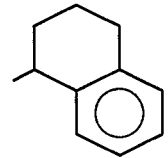 |
| 163 | CH₃ | H |  | H | H | —NH— | 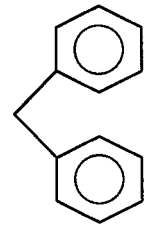 |

TABLE-continued

| Compound No. | R¹ | R² | R³ | R⁴ | R⁵ | Y | Z |
|---|---|---|---|---|---|---|---|
| 164 | CH₃ | H | CH₂CH=CH₂ | H | H | —NH— | 4-propylphenyl |
| 165 | CH₃ | H | CH₂CH=CH₂ | H | H | —N(CH₃)— | CH₃ |
| 166 | CH₃ | H | CH₂CH=CH₂ | H | H | —N(CH₃)— | 4-ethylphenyl |
| 167 | CH₃ | H | CH₂CH=CH₂ | H | H | —N(CH₃)— | 4-propylphenyl |
| 168 | CH₃ | H | CH₂CH=CH₂ | H | H | —N(CH₂CH₃)— | 4-isopropylphenyl |
| 169 | CH₃ | H | CH₂C(CH₃)=CH₂ | H | H | —NH— | 4-isopropylphenyl |
| 170 | CH₃ | H | CH₂CH=CHF | H | H | —NH— | 4-propylphenyl |
| 171 | CH₂CH=CH₂ | H | CH₂CH=CH₂ | H | H | —N(CH₃)— | CH₃ |
| 172 | CH₃ | H | CH₂CH=CH₂ | H | H | —NH— | 5-ethylfuran-2-yl |
| 173 | CH₃ | H | CH₂CH=CH₂ | H | H | —NH— | 5-pentylfuran-2-yl |
| 174 | CH₃ | H | CH₂CH=CH₂ | H | H | —NH— | 5-ethylthiophen-2-yl |
| 175 | CH₃ | H | CH₂CH=CH₂ | H | H | —NH— | 4-methoxy-substituted propylphenyl |
| 176 | CH₃ | H | CH₂CH=CH₂ | H | H | —NH— | —CH(CH₃)₂ |

TABLE-continued

| Compound No. | R¹ | R² | R³ | R⁴ | R⁵ | Y | Z |
|---|---|---|---|---|---|---|---|
| 177 | CH₃ | H | allyl | H | H | —NH— | —CH₂CH(CH₃)₂ |
| 178 | CH₃ | H | allyl | H | H | —NH— | —C(CH₃)₃ |
| 179 | CH₃ | H | allyl | H | H | —NH— | 2-ethyltetrahydrofuran |
| 180 | CH₃ | H | allyl | H | H | 4-piperidinyl-N— | —OCH₃ |
| 181 | CH₃ | H | allyl | H | H | —N(C₂H₄OC₂H₅)— | —C₂H₄OC₂H₅ |
| 182 | CH₃ | H | allyl | H | H | 2-piperidinyl-N— | CH₃ |
| 183 | CH₃ | H | allyl | H | H | 2,6-dimethylpiperidinyl-N— | CH₃ |
| 184 | CH₃ | H | allyl | H | H | —NH— | —CH(CH₂OCH₃)₂ |
| 185 | CH₃ | H | allyl | H | H | —NH— | trans-4-methoxycyclohexyl |
| 186 | CH₃ | H | allyl | H | H | —NH— | cis-4-methoxycyclohexyl |
| 187 | CH₃ | H | allyl | H | H | —NH— | cis-4-(OCH₂CH₂OCH₂CH₃)cyclohexyl |
| 188 | CH₃ | H | allyl | H | H | —NH— | tetrahydropyran-4-yl |

TABLE-continued

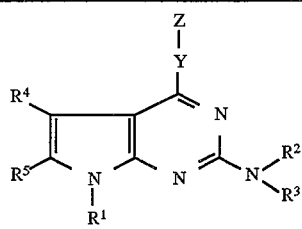

| Compound No. | R¹ | R² | R³ | R⁴ | R⁵ | Y | Z |
|---|---|---|---|---|---|---|---|
| 189 | CH₃ | H | ~⚋ | H | H | —N(CH₃)— | (trans-4-methoxycyclohexyl) |
| 190 | CH₃ | H | ~⚋ | H | H | —NH— | (3-propoxy-2,5-dimethoxyphenyl) | wherein F₂BH[1], [2] and MMTr[3] represent

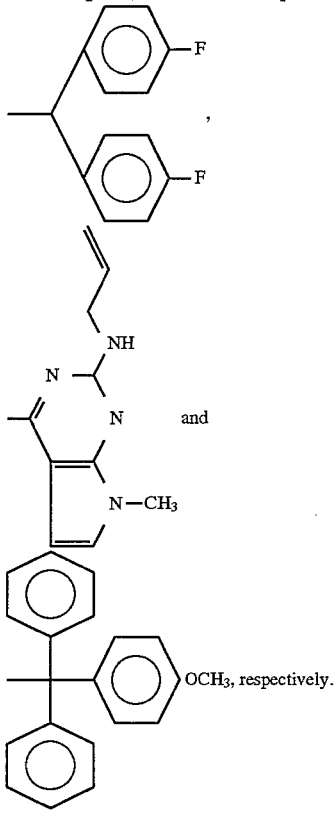

OCH₃, respectively.

The pyrrolo[2,3-d]pyrimidine derivatives in accordance with the present invention may be acid addition salts, and suitable examples of acids forming such salts include inorganic acids such as hydrochloric acid, hydrobromic acid, sulfuric acid, phosphoric acid, nitric acid, boric acid, carbonic acid, and the like; organic carboxylic acids such as formic acid, acetic acid, propionic acid, citric acid, succinic acid, maleic acid, oxalic acid, tartaric acid, maleic acid, fumaric acid, and the like; and organic acids such as methanesulfonic acid, ethanesulfonic acid, benzenesulfonic acid, p-toluene-sulfonic acid, camphorsulfonic acid, and the like.

According to the present invention, a pyrrolo[2,3-d]pyrimidine derivative and pharmaceutically acceptable acid addition salt thereof can be produced by reacting a halogenated pyrrolo[2,3-d]pyrimidine derivative, or acid addition salt, represented by the general formula II

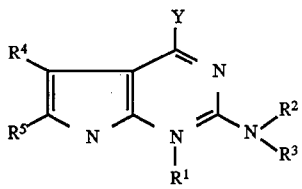

(II)

wherein $R^1$, $R^2$, $R^3$, $R^4$ and $R^5$ have the meanings defined in the formula I of claim 1, and X represents a halogen atom with an amine compound represented by the general formula III

  (III)

wherein Y and Z have the same meanings as defined in the above formula I, followed by mixing with an inorganic or organic acid, if necessary.

The halogenated pyrrolo[2,3-d]pyrimidine derivative represented by the formula II (wherein $R^1$ to $R^5$ have the meanings defined above in connection with the $R^1$ to $R^5$ in the formula I and X represents a halogen atom) may be a novel or known compound. With respect to the known compound, a process for producing same is also known in the art (see, for example, F. Seela et al., Liebigs Ann. Chem., 137 (1983); and M. Legraverend et al., Tetrahedron Lett., Vol. 26, 2001 (1985)).

Also a novel compound can be prepared according to a process of producing a similar known compound. Examples of the halogen atom in the halogenated pyrrolo[2,3-d]pyrimidine derivative include a chlorine atom, a bromine atom and an iodine atom. Such atoms are highly reactive, and a pyrrolo[2,3-d]pyrimidine derivative of interest, represented by the formula I, can be produced by reacting such atoms with an amine compound represented by the formula III wherein Y and Z have the meanings defined above in connection with the Y and Z in the formula I.

The amine compound represented by the formula III, as such, is known in the art, or may be produced according to a known process. Suitable specific examples of the above-described amine compound, when Y represents a linking group of the formula:

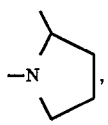

include pyrrolidine, 2-methylpyrrolidine, 2-hydroxymethylpyrrolidine, 2-benzylpyrrolidine, 2-phenylpyrrolidine, 2-carboxypyrrolidine and 2-methoxycarbonylpyrrolidine; when Y represents a linking group of the formula:

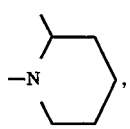

include piperidine, 2-methylpiperidine, 2-hydroxymethylpiperidine, 2-benzylpiperidine, 2-phenylpiperidine, 2-carboxypiperidine and 2-methoxycarbonylpiperidine; when Y represents a linking group of the formula:

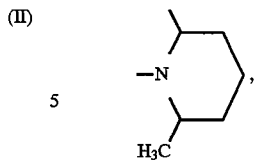

include 2,6-dimethylpiperidine; when Y represents a linking group of the formula:

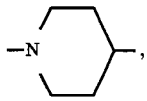

include 4-hydroxypiperidine, 4-methylpiperidine, 4-ethylpiperidine, 4-benzylpiperidine, 4-(4-fluorobenzyl) piperidine, 4-[bis(4-fluorophenyl)methyl]piperidine, 4-phenylpiperidine, 4-acetyloxypiperidine, 4-propanoyloxypiperidine, 4-benzoyloxypiperidine, 4-(4-fluorobenzoyloxy)piperidine, 4-(4-chlorobenzoyloxy)piperidine, 4-(phenylacetyloxy)piperidine, 4-acetylpiperidine, 4-propanoylpiperidine, benzoylpiperidine, 4-(1-methoxyimino)ethylpiperidine, 4-carboxypiperidine, 4-isopropyloxycarbonylpiperidine, 4-methoxypiperidine, 4-ethoxypiperidine, 4-(methylamino)piperidine, 4-(N,N-dimethylamino)-piperidine, 4-(acetylamino)piperidine and 4-(N-methyl-N-acetylamino) piperidine; when Y represents a linking group of the formula:

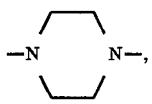

include N-methylpiperazine, N-(2-methoxyethyl) piperazine, N-allylpiperazine, N-phenylpiperazine, N-benzylpiperazine, N-(4-fluorophenyl)piperazine, N-(4-fluorobenzyl)piperazine, N-(2-phenylethyl)piperazine, N-[2-[2-(trifluoromethyl)phenyl]ethyl]piperazine, N-cinnamylpiperazine, N-[bis(4-fluorophenyl)methyl] piperazine, N-acetylpiperazine, N-(4-fluorobenzoyl) piperazine, N-(4-chlorobenzoyl)piperazine, N-(4-fluorophenylacetyl)piperazine and N-cinnamoylpiperazine; and when Y represents a linking group of the formula:

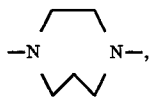

include N-methyl-perhydro[1,4]diazepine, N-allyl-perhydro[1,4]diazepine, N-benzyl-perhydro[1,4]diazepine, N-(2-phenylethyl)perhydro[1,4]diazepine, N-[bis(4-fluorophenyl)methyl]perhydro[1,4]diazepine and N-acetyl-perhydro[1,4]diazepine; when Y represents a linking group of the formula: —NH—, include ammonia, allylamine, 2-methylallylamine, methylamine, isopropylamine, isobutylamine, tert-butylamine, 1,3-dimethoxy-2-propylamine, tetrahydrofurfurylamine, 2-(N,N-dimethylamino)ethylamine, 2-morpholinoethylamine, 2-piperidinoethylamine, 2-(3,5-dimethoxyphenoxy) ethylamine, trans-4-hydroxycyclohexylamine, cyclohexylamine, trans-4-methoxycyclohexylamine, cis-4-methoxycyclohexylamine, trans-4-(2-ethoxyethoxy) cyclohexylamine, 2-tetrahydrofurylamine, 4-tetrahydropyranylamine, benzylamine, 4-fluorobenzylamine, 4-chlorobenzylamine, 4-methoxybenzylamine, 1-phenylethylamine, 1-methyl-1-phenylethylamine, 2-phenylethylamine, 2-(4-fluorophenyl)ethylamine, 2-(4-chlorophenyl)ethylamine, 2-(4-methoxyphenyl)ethylamine, 1,1-diphenylmethylamine, 1,1-bis(4-fluorophenyl)methylamine, cinnamylamine, 1-(1-naphthyl)ethylamine, 1,2,3,4-tetrahydronaphthalene-1-yl amine, furfurylamine, 2-thienylmethylamine, 3-(2-furyl)propylamine; when Y represents a linking group of the formula: —N(CH$_3$)—, —N(C$_2$H$_5$)— or —N(CH$_2$CH$_2$OCH$_2$CH$_3$)—, include dimethylamine, diethylamine, N-methylbenzylamine, N-methyl(2-phenylethyl)amine, N-ethylbenzylamine, N-methyl(1-phenylethyl)amine, N-ethyl-(1-phenylethyl)amine, N-methylallylamine and Bis(2-ethoxyethyl)amine; when Y and Z taken together represent a group —Y—Z, include morpholine and thiomorpholine.

The above-described reaction can be conducted, for example, by reacting one equivalent of a halogenated pyrrolo[2,3-d]pyrimidine derivative represented by the formula II with 1 to 30 equivalents of a amine compound represented by the formula III in the absence or presence of a solvent. If necessary, a base also may be present in the reaction system, and examples of the base include inorganic bases such as sodium hydroxide, potassium hydroxide, sodium carbonate and potassium carbonate, and organic bases such as triethylamine, diethylaniline, dimethylaniline and pyridine.

The reaction temperature is from −20° to 300° C., preferably from a room temperature to 200° C. and the reaction time is usually 72 hours or less.

Examples of the reaction solvent include halogenated hydrocarbons such as dichloromethane, chloroform, trichloroethane and carbon tetrachloride; aromatic hydrocarbons such as benzene, toluene and xylene; alcohols such as methanol, ethanol, isopropyl alcohol, butanol and tert-butanol; ethers such as diethyl ether, tetrahydrofuran and dioxane; and aprotic polar solvents such as dimethylformamide, dimethylacetamide, dimethylsulfoxide and sulfolane.

After the completion of the reaction, the desired product, a pyrrolo[2,3-d]pyrimidine derivative represented by the formula I, can be isolated by general separating and purifing procedure, i.e., concentration, extraction, recrystallization, and chromatography, etc. The compound I can be also converted to a pharmaceutically acceptable acid addition salt according to a conventional method.

The entire steps of the reaction, including general steps utilized for producing the above-described starting material of the formula II, are as follows:

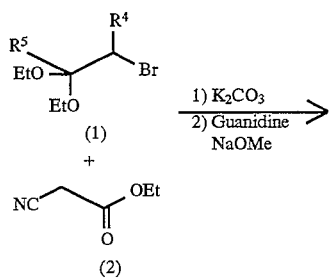

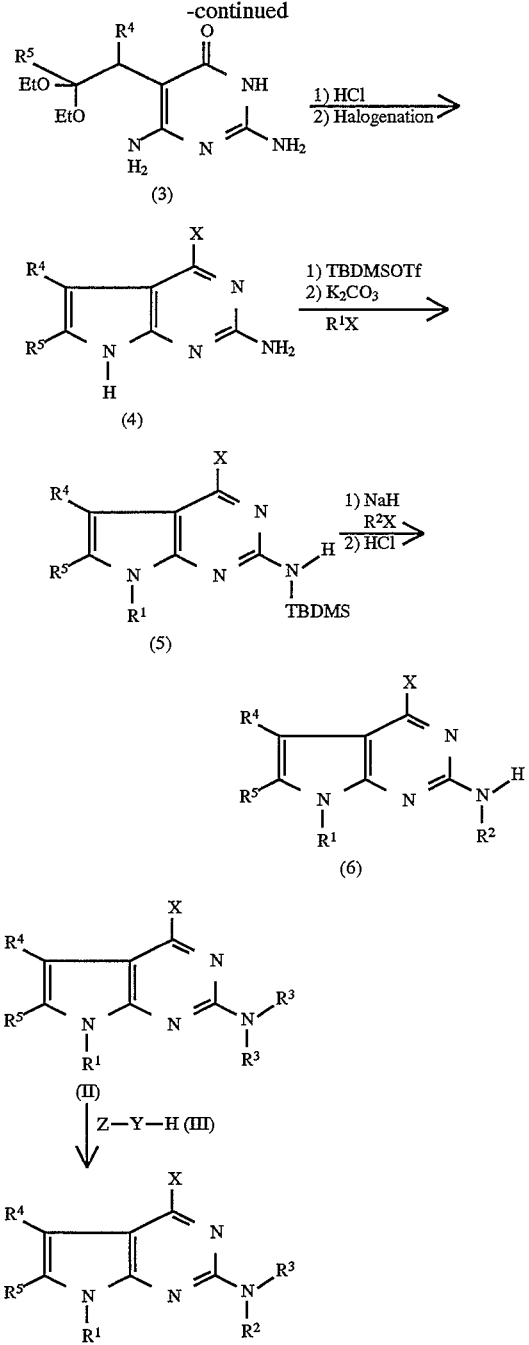

wherein R$^1$, R$^2$, R$^3$, R$^4$ and R$^5$, as well as X, Y and Z, have the meanings as defined above, and TBDMSOTf represents tert-butyl-dimethyl-silyl-trifluoromethanesulfonate.

The reaction steps for the compound of formula II are summarized as follows:

The compound of the formula (3) can be obtained by a reaction of acetal (1) with ethyl cyanoacetate (2) in an alkaline condition, following by a ring-closing reaction using guanidine in the presence of a strong base.

The compound of formula (4) can be obtained by a ring-closing reaction of the resulting compound (3) in the presence of hydrochloric acid, followed by a halogenation according to a usual method, e.g., with phosphorus oxychloride.

The compound of formula (5) can be obtained by a silylation of the resulting compound (4) with TBDMSOTf, followed by a reaction with $R^1X$, wherein X is a halogen atom, in an alkaline condition.

The compound of formula (6) can be obtained by a reaction of the resulting compound (5) with $R^5X$ in the presence of a strong base, followed by a desilylation with hydrochloric acid.

The compounds, to which are selectively introduced the substituents $R^1$, $R^2$ and $R^3$, of the formula II can be obtained by a reaction of the final compound (6) with $R^3X$, in the presence of a strong base.

The present compounds exhibit an excellent pharmacological action against hypoxemia associated with various respiratory diseases. It is generally known that, in pneumonopathy, e.g., pneumonectasis, bronchitis, bronchial asthma, interstitial preumonia and pneumonophthisis, the partial pressure of oxygen ($PaO_2$) in arterial blood lowers according as the pathosis is severer or chronic. In this case, symptoms such as a feeling of fatigue, shortness of breath and choking feeling occur, and in a serious state, dyspnea, cyanosis and a disturbance of consciousness occur.

Therefore, a pharmaceutical preparation capable of raising and improving the $PaO_2$ lowered due to such respiratory diseases has been desired in the art. Further, it is often shown that, in such diseases, the partial pressure of carbon dioxide ($PaCO_2$) in arterial blood increases conversely to a decrease of $PaO_2$, and in this case, there is a need for a pharmaceutical preparation that can not only increase $PaCO_2$ but also decrease $PaO_2$.

The compounds in accordance with the present invention have actions such that they enhance the respiratory function of the lung, that one mainly increases only $PaO_2$, and that another increases $PaO_2$ and decreases $PaCO_2$, at the same time, and thus the present compounds are useful for the treatment of hypoxemia associated with various respiratory diseases.

The pharmacological effect of the compound in accordance with the present invention can be demonstrated by an acute hypoxemia model using an experimental animal. For example, the acute hypoxemia (having a lower $PaO_2$ value) model can be prepared by administering intratracheally a fine powder, such as carbon powder, silica gel, glass beads or dental impression material, in a small animal, e.g., rat, to lower the respiratory function (see, for example, Munakata et al., *Preprints of the 35th Symposium of Japan Society of Anesthesiology*, 179 (1988)). Also the acute hypoxemia (having a lower $PaO_2$ value) model can be prepared by administering intratracheally a mucosa-prophiogistic acid, e.g., acetic acid and crotonic acid. Therefore, the compounds in accordance with the present invention were orally or parenterally administered to the above-described model animal, and the arterial blood was collected after a given period of time and subjected to a measurement of $PaO_2$ (or $PaCO_2$) by a blood gas analyzer. As a result, a significant increase of $PaO_2$ (or decrease of $PaCO_2$) in comparison with that before the administration, was observed.

The pyrrolo[2,3-d]pyrimidine derivative and its acid addition salt in accordance with the present invention can be administered orally or as a parenteral administration such as an intravenous, subcutaneous, intramuscular, percutaneous, intrarectal or other administration.

Examples of the dosage form for the oral administration include tablets, pills, granules, powders, suspensions and capsules.

The tablets can be formulated by a conventional method through the use of, for example, excipients such as lactose, starch and crystalline cellulose; binders such as carboxymethylcellulose, methylcellulose and polyvinylpyrolidone; and disintegrators such as sodium alginate, sodium hydrogencarbonate and sodium laurylsulfate.

Similarly, the pills, powders and granules can be formulated by a conventional method through the use of the above-described excipients, etc. The solutions and suspensions can be formulated by a conventional method through the use of, for example, glycerin esters such as tricaprylin and triacetin and alcohols such as ethanol. The capsules can be formulated by filling a granule, a powder or a solution into a capsule made of gelatin, and the like.

Examples of the dosage form for a subcutaneous, intramuscular and intravenous administration include injections in the form of an aqueous or nonaqueous solution. In the aqueous solution, use is made of, for example, a physiological saline, and the like. In the nonaqueous solution, use is made of, for example, propylene glycol, polyethylene glycol, olive oil, ethyl oleate, and the like. If necessary, preservatives, stabilizers, etc., may be added thereto. The injections can be sterilized by a proper treatment, such as a filtration through the bacterial filter, or by an addition of a bacteriocide.

Examples of the dosage forms for a percutaneous administration include ointments and creams. The ointments and creams can be formulated by a conventional method through the use of fatty oils, such as castor oil and olive oil, petrolatums, etc., in the case of the ointments, and emulsifiers, such as diethylene glycol and sorbitan monofatty acid esters, etc., in the case of the creams.

Conventional suppositories, such as gelatin soft capsules, may be used for a rectal administration.

Although the dosage of the pyrrolo[2,3-d]pyrimidine derivative of the present invention varies depending upon the kind of disease, administration path, age and sex of patient, and severity of disease, etc., it is usually 1 to 500 mg/day/adult.

All of the compounds provided by the present invention (testing substances) have more than 2 g/kg (rat, P.O.) of $LD_{50}$.

EXAMPLES

The present invention will now be described in more detail with reference to the following Examples.

Reference Example

Synthesis of 2-allylamino-4-chloro-7-methyl-7H-pyrrolo[2,3-d]pyrimidine

Procedure A:

A mixture of 5.00 g (29.6 mmol) of 2-amino-4-chloro-7H-pyrrolo[2,3-d]pyrimidine, 10.08 g (1.1 eq.) of p-anisylchlorodiphenylmethane, and 4.96 ml (12 eq.) of triethylamine in 65 ml of dimethylformamide (DMF) was stirred at room temperature for 30 min. After cooling to 0° C., 4.50 ml (2.44 eq.) of methyliodide and 3.00 g (2.53 eq.) of sodium hydride were added in order, and the mixture was stirred for one hour. And then, 5.36 ml (1.5 eq.) of allyl iodide and 2.00 (2.5 eq.) of sodium hydride were added to the reaction mixture followed by additional one hour stirring at 0° C. Finally 200 ml of 2N hydrochloric acid and 100 ml of diethyl ether were added and stirred for one hour at room temperature. The reaction mixture was neutralized with sodium bicarbonate and extracted with three portion of 100 ml of ethylacetate. The combined organic layer was washed with brine, dried over anhydrous magnesium sulfate. The solvents were removed in vacuo. The residual oily mixture was purified with silica-gel column chromatography (hexane: ethylacetate=8:1 as elutant), to give 3.51 g (53.1%) of 2-allylamino-4-chloro-7-methyl-7H-pyrrdo[2,3-d]pyrimidine.

Procedure B:

To 300 ml of methylene chloride was added 26.9 g (159.5 mmol) of 2-amino-4-chloro-7H-pyrrolo[2,3-d]pyrimidine and 111 ml (5 eq.) of triethylamine, and the mixture was stirred at −30° C. Then 36.7 ml (1.1 eq.) of tert-butyldimethylsillyl trifluoromethane sulfonate was slowly dropwised to the mixture, and reacted for 1.5 hours. The crystals were completely dissolved to form a light brown solution. The mixture was allowed to worm to room temperature and filtrated with 200 g of silica-gel on a glass-filter. The filtrate and an elute eluted with 1 l of methylene chloride was combined. After evaporation of the solution, to the oily residue was added 300 ml of aqueous 1N NaOH, and the aqueous solution was extracted with hexane (500 ml×4). The combined organic layer was washed with water and brine in order, dried over anhydrous magnesium sulfate, and removed the solvents in vacuo. The resulting crystals were recrystallized from hexane, to give 35.27 g (yield 78.2%) of 2-tert-butyl-dimethylsilylamino-4-chloro-7H-pyrrolo[2,3-d]pyrimidine in the form of light brown plates (m.p. 114° C.)

Physical Property:

$^1$H-NMR (CDCl$_3$) δ:

0.30(s, 6H), 0.98(s, 9H), 4.5(br-s, 1H)

6.4H(m, 1H) 6.9(m, 1H), 8.3(br-s, 1H)

Then, 44.0 g (115.6mmol) of tert-butyldimethylsilylamino-4-chloro-7H-pyrrolo[2,3-d]pyrimidine and 13.5 ml (1.4 eq.) of methyl iodide in 150 ml of DMF, and 34.40 g (1.6 eq.) of potassium carbonate was reacted at room temperature for 15 hours with vigorous stirring. After addition of water to the reaction mixture, the aqueous solution was extracted with hexane (200 ml×4), washed with brine, and dried over anhydrous magnesium sulfate. The solvents were removed in vacuo, to give 45.87 g (154.5 mmol) (quantitative yield) of 2-ter-butyl-dimethylsilylamino-4-chloro-7-methyl-7H-pyrrolo[2,3-d]pyrimidine in the form of light yellow crystals. Under nitrogen atmosphere the crystals and 21.19 ml (1.5 eq.) of allyl iodide were dissolved in 300 ml of DMF, and the reaction mixture was cooled to 0° C. with vigorous stirring, then 9.27 g (1.5 eq.) of sodium hydride (60%), thoroughly washed by hexane, was added to that as hexane suspension.

The mixture was stirred for 10 min., and then 300 ml of water was slowly added to stop the reaction. The aqueous solution was extracted with hexane (300 ml×4), the combined organic layer was washed with water and brine, and dried over anhydrous magnesium sulfate. After evaporation, 53.5 g of a yellow oily residue was given. The residue was dissolved in 30 ml of diethylether, acid to the solution 50 ml of concentrated hydrochloric acid was added at 0° C. with stirring, and the mixture was reacted for 10 min. After the reaction was completed, to the solution was added diethyl-ether (100 ml×2) to separate the organic layer. The aqueous layer was diluted with 200 ml of ice-water, and then neutralized with a 5N NaOH aqueous solution.

The Resulting precipitate was extracted with ethylacetate (250 ml×3), the extract was washed with water and brine, dried over anhydrous magnesium sulfate, and evaporated, to give 33.57 g (yield 97.6%) of 2-allylamino-4-chloro-7-methyl-7H-pyrrolo[2,3-d]pyrimidine in the form of light yellow crystals.

The crystals were recrystallized from ethylalcohol to give 32.57 g (yield 94.0%) of the above-described compound as yellowish white plates (m.p. 113°–114° C.)

Physical Properties:

$^1$H-NMR (CDCl$_3$), δ: 3.67(s, 3 H), 4.0–4.2(m, 2H), 3.9–5.4(m, 3H). 5.75–6.25(m, 1H), 6.34(d, 1H, J=3.5 Hz), 6.77(d, 1H, J=3.5 Hz).

Elemental analysis: for $C_{10}H_{11}N_4Cl$, Calculated: C, 53.94; H, 4.98; N, 25.16 Found: C, 53.90; H, 4.98; N, 25.11

Example 1

Synthesis of (±)-2-allylamino-7-methyl-4-(1-phenylethyl-amino]-7H-pyrrolo[2,3-d]pyrimidine and its hydrochloride (156)

To 70 ml of n-butylalcohol was added 32.5 g (146.0 mmol) of 2-allylamino-4-chloro-7-methyl-7H-pyrrolo[2,3-d]pyrimidine prepared in Reference Example, 26.22 g (1.3 eq.) of potassium carbonate and 88 g (5.0 eq.) of (±)-phenyl-ethylamine, the mixture was stirred in an autoclave equipped with a stirrer at 165° C. (5 atm) for 5 hours. After cooling to room temperature, 400 ml of water was added, and the mixture was extracted with ethylacetate (250 ml×3). Combined organic layer was washed with water and brine, dried over anhydrous magnesium sulfate, and then the solvents and unreacted (±)-phenylethyl-amine were removed in vacuo. The red oily residue was crystallized with isopropylalcohol, to give 40.38 g (yield 90.0%) of (±)-2-allylamino-7-methyl-4-(1-phenylethyl-amino)-7H-pyrrolo [2,3-d]pyrimidine [(156) free base] in the form of crude crystals. They were recrystallized from isopropylalcohol to give 37.56 g (yield 83.7%) of colorless needles (m.p. 112°–112.5° C.). Then 30.00 g of the free base was dissolved in 800 ml of diethylether, and a saturated hydrochloric acid ethereal solution was added to form hydrochloride.

The diethylether and excess hydrochloric acid were evaporated and the resulting oily residue was crystallized with acetone.

The crystals were washed with acetone, and dried in vacuo at 80° C., to give 33.08 g (yield from the free base, 98.6%) of (±)-2-allylamino-7-methyl-4-(1-phenylethylamino)-7H-pyrrolo[2,3-d]pyrimidine hydrochloride [(156) HCl.salt] in the form of colorless crystals (m.p. 167°–170° C.).

Physical Properties

The Free Base $^1$H-NMR (CDCl$_3$) δ:

1.60 (d, 3H, J=6,8), 3.60(s, 3H), 4.0(t, 2H, J=5.7), 4.65 (br-t, 1H, J=5,7), 4.95(br-s, 1H), 4.9–5.4(m, 2H), 5.43(t, 1H, J=6.8), 5.7–6.2(m, 1H), 6.11(d, 1H, J=3.5), 6.54(d, 1H, J=3.5), 7.2–7.5(m, 5H)

IR(KBr) vmax, cm$^{-1}$ 3240, 1620, 1560, 1450, 1285

UV(EtOH) λmax, nm 295, 228

Elemental analysis: for $C_{15}H_{21}N_5$, Calculated: C, 70.33; H, 6.89; N, 22.78. Found: C, 70.38; H, 7.01; N, 22.63.

The Hydrochloride

IR(KBr) vmax, cm$^{-1}$ 3240, 1620, 1560, 1450, 1285

UV(EtOH) λmax, nm 296, 236, 207

Elemental analysis: for $C_{18}H_{22}N_5Cl$, Calculated: C, 62.87; H, 6.45; N, 20.37; Cl, 10.26 Found: C, 62.84; H, 6.40; N, 20.23; Cl, 10.29.

In the following Examples, the compounds of the present invention were prepared by the procedures described in Example 1, using corresponding starting materials and reactants, respectively, as well as reaction solvents and coexisting bases indicated in the following tables, and each reaction was performed under the condition, i.e., reaction temperature, reaction times, and reaction vessel, indicated in said tables.

| Ex. No. | Compound No. | H-NMR data of free base, (CDCl₃) δ (ppm) | Yield of free base (%) | Type of salt M.P. of acid addition salt Recrystallization solvent | UV of acid addition salt EtOH λ max (nm) | Reaction solvent Coexisting base | Reaction temp. Reaction time Reaction vessel |
|---|---|---|---|---|---|---|---|
| 2 | 101 | 2.47(t-like, 4H, J=5Hz), 3.7–4.1(m, 6), 4.25(s, 1H), 4.9–5.3(m, 3H), 5.7–6.1(m, 1H), 6.28(d, 1H, J=3.7Hz), 6.70(d, 1H, J=3.7Hz), 6.8–7.5(m, 9H) | 71 | HCl.salt 180–184° C. (dec.) i-PrOH | 299 233 207 | n-BuOH K₂CO₃ | 120° C. 14 h B |
| 3 | 103 | 2.46(t-like, 4H, J=5Hz), 2.9–3.0(m, 3H), 3.61(s, 3H), 3.88(t-like, 4H, J=5Hz), 4.23(s, 1H), 4.3–4.7(m, 1H), 6.23(d, 1H, J=3.6Hz), 6.56(d, 1H, J=3.6), 6.8–7.5(m, 8H) | 74 | HCl.salt | — | n-BuOH K₂CO₃ | 120° C. 5 h B |
| 4 | 104 | 1.9–2.1(m, 4H), 3.62(s, 3H), 3.6–3.9(m, 4H), 4.0–4.2(m, 2H), 4.6(br-s, 1H), 5.0–5.4(m, 2H), 5.8–6.3(m, 1H), 6.35(d, 1H, J=3.5Hz), 6.54(d, 1H, J=3.5Hz) | 74 | HCl.salt 193–195° C. i-PrOH | 302 267 237 | n-BuOH K₂CO₃ | 110° C. 8 h B |
| 5 | 105 | 1.8–2.0(m, 4H), 2.7(m, 1H), 3.4(m, 1H), 3.64(s, 3H), 3.8(m, br, 3H), 4.17(m, 2H), 4.7(br, 1H), 5.0–5.4(m, 2H), 5.8–6.3(m, 1H), 6.38(d, 1H, J=3.5Hz), 6.57(d, 1H, J=3.5Hz), 7.25(s, 5H) | 70 | HCl.salt 150–153° C. i-PrOH | 299 237 206 | none K₂CO₃ | 145° C. 20 h B |
| 6 | 106 | 1.9–2.7(m, 4H), 3.57(s, 3H), 3.5–4.4(m, 5H), 4.8(br-1H), 4.9–5.4(m, 2H), 5.7–6.2(m, 1H), 6.41(d, 1H, J=3.5Hz), 6.54(d, 1H, J=3.5Hz), 9.4(br, 1H) | 21 | fumarate EtOH | — | n-BuOH K₂CO₃ | 100° C. 4 h B |
| 7 | 107 | 1.5–2.0(m, 6H), 3.61(s, 3H), 3.8–3.95(m, 4H), 4.08(t-like, 2H, J=5.5Hz), 4.6(br, 1H), 4.95–5.4(m, 2H), 5.8–6.3(m, 1H), 6.31(d, 1H, J=3.5Hz), 6.57(d, 1H, J=3.5Hz) | 100 | HCl.salt 161–162° C. i-PrOH | — | n-BuOH — | 110° C. 6 h B |
| 8 | 109 | 1.6–1.7(br, 4H), 1.8–2.5(br, 2H), 3.1(m, 1H), 3.61(s, 3H), 4.05(m, 2H), 4.6(br, 1H), 4.8(br, 1H), 5.0–5.3(m, 2H), 5.8–6.1(m, 1H), 6.1(br, 1H), 6.16(d, 1H, J=3.5Hz), 6.51(d, 1H, J=3.5Hz), 7.30(s-like, 5H) | 45 | fumarate 158–159° C. EtOH | 233 206 | — K₂CO₃ | 150° C. 35 h B |
| 9 | 110 | 1.1–1.9(m, 5H), 2.54(d, 2H, J=6.6Hz), 2.92(t, 2H, J=11Hz), 3.60(s, 3H), 4.06(t, 2H, J=6Hz), 4.5–4.7(m, 3H), 4.9–5.4(m, 2H), 5.7–6.2(m, 1H), 6.27(d, 1H, J=3.5Hz), 6.56(d, 1H, J=3.5Hz), 7.0–7.4(m, 5H) | 100 | — | — | n-BuOH K₂CO₃ | 120° C. 5 h B |
| 10 | 113 | 1.5–2.1(m, 4H), 2.15(s, 3H), 2.4–2.8(m, 1H), 2.9–3.35(m, 2H), 3.60(s, 3H), 4.07(t, 2H, J=6Hz), 4.5–4.9(m, 3H), 5.0–5.4(m, 2H), 5.7–6.3(m, 1H), 6.28(d, 1H, J=3.5Hz), 6.58(d, 1H, J=3.5Hz) | 100 | fumarate 164–166° C. EtOH | — | n-BuOH K₂CO₃ | 120° C. 8 h B |
| 11 | 114 | 1.4–2.0(m, 7H), 2.2–2.65(m, 1H), 2.8–3.2(m, 2H), 3.61(s, 3H), 3.82(s, 3H), 4.07(t, 2H, J=6Hz), 4.5–5.4(m, 5H), 5.8–6.3(m, 1H), 6.29(d, 1H, J=3.5Hz), 6.58(d, 1H, J=3.5Hz) | 30 | fumarate 133–134° C. EtOH | — | n-BuOH K₂CO₃ | 120° C. 4 h B |
| 12 | 115 | 1.3–2.1(m, 4H), 2.3–2.7(m, 1H), 2.9–4.7(br, 1H), 2.95–3.4(m, 2H), 3.58(s, 3H), 3.8–4.1(m, 2H), 4.3–4.8(m, 2H), 4.9–5.4(m, 2H), 5.6(br-t, 1H, J=6Hz), 5.8–6.3(m, 1H), 6.29(d, 1H, J=3.5Hz), 6.67(d, 1H, J=3.5Hz) | 98 | — | — | n-BuOH K₂CO₃ | 80° C. 38 h B |
| 13 | 116 | 1.24(d, 6H, J=6.2Hz), 1.5–2.2(m, 4H), 2.3–2.7(m, 1H), 3.0–3.4(m, 2H), 3.63(s, 3H), 3.9–4.2(m, 2H), 4.3–5.4(m, 6H), 5.8–6.4(m, 1H), 6.30(d, 1H, J=3.7), 6.60(d, 1H, J=3.7Hz) | 30 | fumarate 151–153° C. EtOH | — | n-BuOH K₂CO₃ | 120° C. 4 h B |
| 14 | 117 | 1.3–2.15(m, 4H), 3.38(ddd, 2H, J=13Hz, 9.4Hz, 3.3Hz), 3.61(s, 3H), 3.75–4.8(m, 7H), 4.95–5.35(m, 2H), 5.85–6.2(m, 1H), 6.29(d, 1H, J=3.6Hz), 6.59(d, 1H, J=3.6) | 81 | fumarate 183–185° C. EtOH | 301 271 233 | n-BuOH K₂CO₃ | 120° C. 4 h B |
| 15 | 118 | 1.21(t, 3H, J=7.0Hz), 1.3–2.1(m, 4H), 3.2–3.7(m, 5H), 3.61(s, 3H), 3.9–4.4(m, 4H), 4.7(br-t, 2H, J=6Hz), 4.9–5.35(m, 2H), 5.7–6.3(m, 1H), 6.29(d, 1H, J=3.6Hz), 6.57(d, 1H, J=3.6Hz) | 30 | fumarate 163–165° C. EtOH | 300 272 233 | n-BuOH K₂CO₃ | 120° C. 4 h B |
| 16 | 119 | 1.5–2.2(m, 4H), 2.06(s, 3H), 3.3–3.85(m, 2H), 3.62(s, 3H), 3.9–4.4(m, 4H), 4.68(br-t, 1H, J=6.2Hz), 4.85–5.35(m, 3H), 5.75–6.2(m, 1H), 6.28(d, 1H, J=3.7Hz), 6.60(d, 1H, J=3.7Hz) | 30 | fumarate 164–166° C. i-PrOH | 302 271 234 | n-BuOH K₂CO₃ | 120° C. 4 h B |
| 17 | 120 | 1.8–2.3(m, 4H), 3.63(s, 3H), 3.55–3.9(m, 2H), 4.0–4.4(m, 4H), 4.69(br-t, 1H, J=6.2), 4.95–5.45(m, 3H), 5.75–6.25(m, 1H), 6.31(d, 1H, J=3.7Hz), 6.61(d, 1H, J=3.7Hz), 6.95–7.2(m, 2H), 7.9–8.2(m, 2H) | 30 | fumarate 159–164° C. EtOH | 301 271 233 204 | n-BuOH K₂CO₃ | 120° C. 4 h B |
| 18 | 121 | 1.16(t, 3H, J=7.3Hz), 1.2–1.7(m, 2H), 1.8–2.3(m, 2H), 2.4–3.3(m, 5H), 3.62(s, 3H), 4.07(t-like, 2H, J=5.7Hz), 4.5–4.85(m, 3H), 5.0–5.4(m, 2H), 5.8–6.3(m, 1H), 6.30(d, 1H, J=3.6Hz), 6.58(d, 1H, J=3.6Hz) | 88 | HCl.salt 185–200° C. i-PrOH | — | n-BuOH K₂CO₃ | 120° C. 4 h B |
| 19 | 122 | 1.1–1.2(m, 5H), 1.96(s, 3H), 2.9–3.35(m, 2H), 3.62(s, 3H), 3.9–4.2(t-like, 2H, J=6Hz), 4.5–4.8(m, 3H), 5.0 . 5.4(m, 2H), 5.4(br, 1H); 5.8–6.3(m, 1H), 6.28(d, 1H, J=3.5Hz), 6.60(d, 1H, J=3.5Hz) | 77 | HCl.salt 156–158° C. i-PrOH | — | n-BuOH K₂CO₃ | 120° C. 4 h B |
| 20 | 123 | 1.2–2.7(m, 7H), 2.30(s, 6H), 2.8–3.2(m, 2H), 3.62(s, 3H), 4.08(t-like, 2H, J=6Hz), 4.5–4.99(m, 3H), 4.95–5.4(m, 2H), 5.8–6.3(m, 1H), 6.31(d, 1H, J=3.5Hz), 6.59(d, 1H, J=3.5Hz) | 96 | HCl.salt i-PrOH | — | n-BuOH K₂CO₃ | 120° C. 6 h B |
| 21 | 124 | 3.63(s, 3H), 3.6–4.0(m, 8H), 4.08(t-like, 2H, J=6Hz), 4.7(br, 1H), 4.95–5.4(m, 2H), 5.7–6.3(m, 1H), 6.28(d, 1H, J=3.5Hz), 6.61(d, 1H, J=3.5Hz) | 100 | HCl.salt 159–161° C. i-PrOH | — | n-BuOH — | 80° C. 14 h B |
| 22 | 125 | 2.6–2.8(m, 4H), 3.62(s, 3H), 4.0–4.3(m, 3H), | 100 | HCl.salt | 302 | n-BuOH | 120° C. |

-continued

| Ex. No. | Compound No. | H-NMR data of free base, (CDCl₃) δ (ppm) | Yield of free base (%) | Type of salt M.P. of acid addition salt Recrystallization solvent | UV of acid addition salt EtOH λ max (nm) | Reaction solvent Coexisting base | Reaction temp. Reaction time Reaction vessel |
|---|---|---|---|---|---|---|---|
| | | 4.8(br-t, 1H, J=6Hz), 5.0–5.4(m, 2H), 5.8–6.3(m, 1H), 6.23(d, 1H, J=3.5Hz), 6.61(d, 1H, J=3.5Hz) | | 174–176° C. i-PrOH | 237 206 | K₂CO₃ | 6 h B |
| 23 | 126 | 2.33(s, 3H), 2.50(t, 4H, J=5Hz), 3.62(s, 3H) 3.91(t, 4H, J=5Hz), 4.08(t-like, 2H, J=6Hz), 4.7(br-t, 1H, J=7Hz), 4.95–5.4(m, 2H), 5.75–6.3(m, 1H), 6.30(d, 1H, J=3.7Hz), 6.50(d, 1H, J=3.7Hz) | 100 | HCl.salt 190–195° C. i-PrOH | — | n-BuOH K₂CO₃ | 100° C. 6 h B |
| 24 | 129 | 3.20(t, 4H, J=5Hz), 3.6(s, 3H), 3.8–4.1(m, 6H), 4.67(br-t, 1H, J=6Hz), 4.9–5.3(m, 2H), 5.75–6.1(m, 1H), 6.33(d, 1H, J=3.6Hz), 6.62(d, 1H, J=3.6Hz), 6.7–7.0(m, 4H) | 89 | HCl.salt 190–194° C. EtOH | 301 239 206 | n-BuOH K₂CO₃ | 120° C. 27 h B |
| 25 | 130 | 2.53(t, 4H, J=5Hz), 3.54(s, 2H), 3.61(s, 3H), 3.7–4.1(m, 6H), 4.6(br-t, 1H, J=6Hz), 4.85–5.3(m, 2H), 5.6–7.2(m, 1H), 6.27(d, 1H, J=3.5Hz), 6.57(d, 1H, J=3.5Hz), 7.0–7.3(m, 5H) | 26 | — | — | n-BuOH K₂CO₃ | 120° C. 17 h B |
| 26 | 131 | 2.50(t, 4H, J=5Hz), 3.47(s, 2H), 3.60(s, 3H), 3.7–4.2(m, 6H), 4.69(br-t, 1H, J=6Hz), 4.9–5.4(m, 2H), 5.76–6.25(m, 1H), 6.26(d, 1H, J=3.5Hz), 6.56(d, 1H, J=3.5Hz), 6.8–7.45(m, 4H) | 89 | HCl.salt 158–163° C. EtOH/n-hexane | 302 236 206 | n-BuOH K₂CO₃ | 120° C. 18 h B |
| 27 | 132 | 2.4–2.8(m, 6H), 2.8–3.1(m, 2H), 3.62(s, 3H), 3.7–4.2(m, 6H), 4.71(br-t, 1H, J=6), 4.9–5.4(m, 2H), 5.75–6.3(m, 1H), 6.31(d, 1H, J=3.7), 6.60(d, 1H, J=3.7), 7.2–7.7(m, 4H) | 83 | HCl.salt 160–163° C. i-PrOH/EtOH | 304 237 207 | n-BuOH K₂CO₃ | 120° C. 15 h B |
| 28 | 133 | 2.46(t-like, 4H, J=5Hz), 3.61(s, 3H), 3.75–4.15(m, 6H), 4.23(s, 1H), 4.5–4.8(m, 1H), 4.95–5.4(m, 2H), 5.8–6.2(m, 1H), 6.23(d, 1H, J=3.5Hz), 6.56(d, 1H, J=3.5Hz), 7.1–6.9(m, 4H), 7.5–7.2(m, 4H) | 77 | HCl.salt 166–169° C. i-PrOH | 302 238 206 | n-BuOH K₂CO₃ | 120° C. 14 h B |
| 29 | 135 | 3.63(s, 6H), 3.9–4.25(m, 12H), 4.7(br-t, 2H, J=6Hz), 4.95–5.4(m, 4H), 5.8–6.3(m, 2H), 6.34(d, 2H, J=3.7Hz), 6.61(d, 2H, J=3.7Hz) | 87 | HCl.salt 170–175° C. (dec) | — | n-BuOH K₂CO₃ | 100° C. 24 h B |
| 30 | 136 | 2.46(t-like, 4H, J=5Hz), 3.09(s, 3H), 3.61(s, 3H), 3.87(t-like, 4H, J=5Hz), 4.15–4.4(m, 3H), 4.9–5.3(m, 2H), 5.6–6.1(m, 1H), 6.21(d, 1H, J=3.6Hz), 6.55(d, 1H, J=3.6Hz), 6.8–7.6(m, 8H) | 58 | HCl.salt 155–161° C. i-PrOH | 302 241 206 | n-BuOH K₂CO₃ | 120° C. 8 h B |
| 31 | 137 | 2.45(t-like, 4H, J=5Hz), 3.60(s, 3H), 3.85(t-like, 4H, J=5Hz), 4.15–4.3(m, 5H), 5.0–5.3(m, 4H), 5.7–6.1(m, 2H), 6.21(d, 1H, J=4Hz), 6.55(d, 1H, J=4Hz), 7.1–6.9(m, 4H), 7.5–7.2(m, 4H) | 54 | — | — | DMF K₂CO₃ | 100° C. 5 h B |
| 32 | 138 | 1.4–2.3(m, 4H), 2.08(s, 3H), 2.38(s, 3H), 3.5–3.85(m, 2H), 3.73(s, 3H), 4.0–4.4(m, 2H), 4.66(d, 2H), J=5.3Hz), 4.8–5.35(m, 3H), 5.7–6.2(m, 1H), 6.43(d, 1H, J=3.6Hz), 6.89(d, 1H, J=3.6) | 30 | fumarate — EtOH | — | n-BuOH K₂CO₃ | 120° C. 4 h B |
| 33 | 139 | 2.03(t-like, 4H, J=5Hz), 3.5–3.3(m, 9H), 3.74(s, 3H), 5.8(br-s, 1H), 6.17(d, 1H, J=3.6Hz), 6.51(d, 1H, J=3.5Hz), 6.72(d, 2H, J=9Hz), 7.3–6.9(m, 17H) | 60 | — | — | n-BuOH K₂CO₃ | 120° C. 5 h B |
| 34 | 140 | 0.90(t, 3H, J=7Hz), 0.95(t, 3H, J=7Hz), 1.4–2.04(m, 4H), 2.46(t-like, 4H, J=5Hz), 3.2–3.5(m, 2H), 3.74–4.1(m, 6H), 4.23(s, 1H), 4.7(br-s, 1H), 6.22(d, 1H, J=4Hz), 6.59(d, 1H, J=4Hz), 6.8–7.15(m, 4H), 7.2–7.5(m, 4H) | 94 | HCl.salt 181–189° C. EtOH | — | n-BuOH K₂CO₃ | 120° C. 24 h B |
| 35 | 141 | 0.89(t, 3H, J=7Hz), 1.55–2.05(m, 2H), 2.46(t-like, 4H, J=5Hz), 3.75–4.15(m, 8H), 4.23(s, 1H), 4.65(br-t, 1H), 4.95–5.4(m, 2H), 5.75–6.2(m, 1H), 6.23(d, 1H, J=4Hz), 6.60(d, 1H, J=4Hz), 6.85–7.15(m, 4H), 7.2–7.5(m, 4H) | 64 | HCl.salt 129–131° C. i-PrOH | — | DMF K₂CO₃ | 100° C. 14 h B |
| 36 | 142 | 0.2–0.7(m, 4H), 0.9–1.4(m, 1H), 2.46(t-like, 4H, J=5Hz), 3.7–4.15(m, 8H), 4.23(s, 1H), 4.45–4.8(br-s, 1H), 4.95–5.4(m, 2H), 5.75–6.2(m, 1H), 6.25(d, 1H, J=4Hz), 6.73(d, 1H, J=4Hz), 6.85–7.15(m, 4H), 7.2–7.5(m, 4H) | 65 | HCl.salt 165–169° C. EtOH | — | DMF K₂CO₃ | 100° C. 14 h B |
| 37 | 143 | 2.46(t-like, 4H, J=5Hz), 3.75–4.1(m, 6H), 4.24(s, 1H), 4.5–4.7(m, 3H), 4.95–5.35(m, 4H), 5.7–6.2(m, 2H), 6.26(d, 1H, J=4Hz), 6.59(d, 1H, J=4Hz), 6.9–7.1(m, 4H), 7.2–7.5(m, 4H) | 97 | HCl.salt 167–173° C. i-PrOH | — | DMF — | 100° C. B |
| 38 | 145 | 2.46(t-like, 4H, J=5Hz), 3.86(t-like, 4H, J=5Hz), 4.1–4.3(m, 5H), 4.6–4.75(m, 2H), 4.95–5.3(m, 6H), 5.7–6.2(m, 3H), 6.23(d, 1H, J=4Hz), 6.58(d, 1H, J=4Hz), 6.85–7.15(m, 4H), 7.2–7.5(m, 4H) | 73 | — | — | DMF K₂CO₃ | 50° C. 10 h B |
| 39 | 146 | 2.46(t-like, 4H, J=5Hz), 3.88(t-like, 4H, J=5Hz), 4.03(m, 2H), 4.23(s, 1H), 4.7(bs-s, 1H), 4.9–5.3(m, 2H), 5.21(s, 2H), 5.7–6.2(m, 1H), 6.25(d, 1H, J=3.6Hz), 6.55(d, 1H, J=3.6Hz), 6.8–7.5(m, 13H) | 62 | HCl.salt 187–190° C. EtOH | 304 239 209 | DMF K₂CO₃ | 100° C. 6 h B |
| 40 | 148 | 0.1–0.5(m, 4H), 1.0(m, br, 1H), 1.60(d, 3H, J=7Hz), 3.23(2H, dd, J=7Hz, 7Hz), 3.60(3H, s), 4.7(br, 1H), 5.0(br, 1H), 5.4(m, 1H), 6.11(d, 1H, J=3.5Hz), 6.52(d, 1H, J=3.5Hz), 7.2–7.4(m, 5H) | 95 | HCl.salt 118–119° C. acetone-diethylether | 297 235 206 | n-BuOH K₂CO₃ | 130° C. 20 h A |
| 41 | 149 | 3.62(s, 3H), 4.09(t-2H, J=5.5Hz), 4.5–5.2(br, 3H) | 100 | HCl.salt | 302 | aq. | 110° C. |

-continued

| Ex. No. | Compound No. | H-NMR data of free base, (CDCl₃) δ (ppm) | Yield of free base (%) | Type of salt M.P. of acid addition salt Recrystallization solvent | UV of acid addition salt EtOH λ max (nm) | Reaction solvent Coexisting base | Reaction temp. Reaction time Reaction vessel |
|---|---|---|---|---|---|---|---|
| | | 5.0–5.4(m, 2H), 5.8–6.3(m, 1H), 6.16(d, 1H, J=3.5Hz), 6.58(d, 1H, J=3.5Hz) | | 215–223° C. (dec.) i-PrOH/ (i-Pr)₂O | 268 235 207 | ammonia — | 15 h A B |
| 42 | 150 | 1.1–2.2(m, 10H), 3.62(s, 3H), 3.9–4.2(m, 3H), 4.4–4.8(m, 2H), 5.0–5.4(m, 2H), 5.7–6.3(m, 1H), 6.14(d, 1H, J=3.4Hz), 6.56(d, 1H, J=3.4Hz) | 92 | HCl.salt 187–189° C. i-PrOH | 296 235 | — K₂CO₃ | 120° C. 19 h B |
| 43 | 151 | 3.63(s, 3H), 4.0–4.3(m, 4H), 4.7(br, 2H), 4.95–5.4(m, 4H), 5.8–6.3(m, 2H), 6.18(d, 1H, J=3.5Hz), 6.59(d, 1H, J=3.5Hz) | 76 | — | — | n-BuOH — | 100° C. 18 h B |
| 44 | 152 | 2.28(s, 6H), 2.55(t, 2H, J=5.7Hz), 3.5–3.7(m, 4H), 4.0–4.2(m, 2H), 4.7(br-s, 1H), 4.9–5.4(m, 2H), 5.4(br-s, 1H), 5.8–6.3(m, 1H), 6.21(d, 1H, J=3.5Hz), 6.56(d, 1H, J=3.5Hz) | 93 | HCl.salt 199–212° C. (dec.) EtOH | 297 234 | — K₂CO₃ | 110° C. 15 h B |
| 45 | 153 | 1.4–1.8(m, 4H), 2.3–2.7(m, 6H), 3.62(s, 3H), 3.5–3.7(m, 2H), 4.10(m, 2H), 4.6(m, 1H), 5.0–5.4(m, 2H), 5.8–6.2(m, 1H), 6.21(d, 1H, J=3.5Hz), 6.56(d, 1H, J=3.5Hz) | 93 | HCl.salt 210–220° C. (dec.) EtOH | 297 234 | — K₂CO₃ | 130° C. 3 h B |
| 46 | 154 | 2.4–2.7(m, 6H), 3.63(s, 3H), 3.5–3.8(m, 6H), 4.10(br-t, 2H, J=6Hz), 4.8–5.5(m, 4H), 5.6–6.2(m, 1H), 6.20(d, 1H, J=3.5Hz), 6.58(d, 1H, J=3.5Hz) | 60 (dec.) | HCl.salt 205–212° C. EtOH | 296 234 | — K₂CO₃ | 130° C. B |
| 47 | 155 | 3.63(s, 3H), 4.10(t, 2H, J=5.5Hz), 4.6–4.85(m, 3H), 4.9–5.4(m, 3H), 5.7–6.3(m, 1H), 6.12(d, 1H, J=3.5Hz), 6.56(d, 1H, J=3.5Hz), 7.2–7.5(m, 5H) | 94 | HCl.salt 174–178° C. acetone | 295 235 208 | — K₂CO₃ | 130° C. 5 h B |
| 48 | 160 | 1.82(s, 6H), 3.58(s, 3H), 3.67(t, 2H, J=5.3Hz), 4.5(br-t, 1H, J=5.5Hz), 4.85–5.2(m, 2H), 5.5–5.95(m, 1H), 4.06(d, 1H, J=3.5Hz), 6.53(d, 1H, J=3.5Hz), 7.1–7.6(m, 5H) | 91 | HCl.salt 181–200° C. acetone | 297 269 234 207 | n-BuOH K₂CO₃ | 180° C. 16 h A |
| 49 | 161 | 1.75(d, 3H, J=6.6Hz), 3.59(s, 3H), 4.01(br-t, 2H, J=5.2Hz), 4.7(br-t, 1H, J=5.2Hz), 4.9–5.35(m, 3H), 5.7–6.2(m, 1H), 6.0(d, 1H, J=3.5Hz), 6.2(t, 1H, J=7Hz), 6.48(d, 1H, J=3.5Hz), 7.3–8.3(m, 7H) | 70 | HCl.salt 135–140° C. i-PrOH | 294 223 | — K₂CO₃ | 150° C. 6 h B |
| 50 | 162 | 1.7–2.3(m, 4H), 2.83(br-t, 2H, J=6Hz), 3.64(s, 3H), 4.11(br-t, 2H, J=6Hz), 4.7(br-t, 1H, J=6Hz), 4.8–5.4(m, 2H), 5.5(m, 1H), 5.8–6.4(m, 1H), 6.09(d, 1H, J=3.6Hz), 6.56(d, 1H, J=3.6Hz), 7.0–7.5(m, 4H) | 79 | HCl.salt 196–200° C. (dec.) i-PrOH | 297 235 207 | — K₂CO₃ | 130° C. 6 h B |
| 51 | 163 | 3.60(s, 3H), 3.96(t, 3H, J=6Hz), 4.65(br-t, 1H, J=6Hz), 4.9–5.35(m, 3H), 5.65–6.1(m, 1H), 6.12(d, 1H, J=3.5Hz), 6.50(s, 1H), 6.54(d, 1H, J=3.5Hz), 7.2–7.4(m, 10H) | 45 | HCl.salt 183–185° C. i-PrOH | 298 236 208 | — K₂CO₃ | 150° C. 27 h B |
| 52 | 164 | 2.95(t, 2H, J=6.8Hz), 3.62(s, 3H), 3.6–3.95(m, 2H), 4.0–4.2(m, 2H), 4.5–4.9(m, 2H), 4.95–5.4(m, 2H), 5.8–6.3(m, 1H), 6.09(d, 1H, J=3.5Hz), 6.55(d, 1H, J=3.5Hz), 7.2–7.4(m, 5H) | 100 | HCl.salt 152–153° C. i-PrOH | 295 234 207 | — K₂CO₃ | 130° C. 1.5 h B |
| 53 | 165 | 3.29(s, 6H), 3.62(s, 3H), 4.0–4.2(m, 2H), 4.6(br-s, 1H), 5.0–5.4(m, 2H), 5.8–6.3(m, 1H), 6.38(d, 1H, J=3.5Hz), 6.56(d, 1H, J=3.5Hz) | 50 | HCl.salt 175–180° C. EtOH | 299 236 202 | n-BuOH K₂CO₃ | 120° C. 14 h A |
| 54 | 166 | 3.26(s, 3H), 3.62(s, 3H), 4.07(t-like, 2H, J=6Hz), 4.7(br, 1H), 4.96(s, 2H), 4.9–5.4(m, 2H), 5.75–6.3(m, 1H), 6.26(d, 1H, J=3.6Hz), 6.53(d, 1H, J=3.6Hz), 7.2–7.4(m, 5H) | 99 | Fumarate 163–164° C. EtOH | — | n-BuOH — | 100° C. B |
| 55 | 167 | 2.97(dd, 2H, J=7.5, J=9.9Hz), 3.22(s, 3H), 3.63(s, 3H), 3.88(dd, 2H, J=7.5, J=9.9Hz), 4.1(m, 2H), 4.6(br-t, 1H, J=6Hz), 4.95–5.4(m, 2H), 5.8–6.3(m, 1H), 6.35(d, 1H, J=3.5Hz), 6.57(d, 1H, J=3.5Hz), 7.1–7.4(m, 5H) | 74 | HCl.salt 177–183° C. i-PrOH | 299 236 207 | — K₂CO₃ | 140° C. 14 h B |
| 56 | 168 | 1.09(t, 3H, J=7Hz), 1.63(d, 3H, J=7Hz), 3.3–3.7(m, 2H), 3.62(s, 3H), 4.07(dd, 2H, J=5.5Hz, 5.5Hz), 4.7(br-t, like, 1H), 5.0–5.3(m, 2H), 5.8–6.2(m, 1H), 6.25(d, 1H, J=3.5Hz), 6.50(d, 1H, J=7Hz), 6.56(d, 1H, J=3.5Hz), 7.2–7.4(m, 5H) | 49 | — | — | — K₂CO₃ LiI | 150° C. 40 h A |
| 57 | 169 | 1.60(3H, d, J=7Hz), 1.75(3Hz), 3.59(s, 3H), 4.7(s, br, 1H), 3.97(d, 2H, J=6Hz), 4.8(s, 1H), 4.9(s, 1H), 5.1(s, br, 1H), 5.4(m, 1H), 6.11(d, 1H, J=3.5Hz), 6.52(d, 1H, J=3.5Hz), 7.2–7.4(m, 5H) | 80 | HCl.salt 160–164° C. acetone | 296 235 206 | n-BuOH K₂CO₃ | 130° C. 15 h A |
| 58 | 171 | 3.29(s, 6H), 4.07(t-like, 2H, J=6Hz), 4.64(d, 2H, J=5.5Hz), 4.9–5.4(m, 4H), 5.7–6.2(m, 2H), 6.41(d, 1H, J=3.5Hz), 6.59(d, 1H, J=3.5Hz) | 74 | HCl.salt 110–111° C. EtOH | 299 237 207 | n-BuOH K₂CO₃ | 120° C. 16 h B |
| 59 | 172 | 3.63(s, 3H), 4.12(t-like, 2H, J=5.6Hz), 4.76(d, 2H, J=5.6Hz), 4.76(br-s, 1H), 5.08(br-s, 1H), 5.10(dd, 1H, J=1.7, 10.2Hz), 5.26(dd, 1H, J=1.7, 17.2Hz), 5.94–6.08(br-s, 1H), 6.26–6.33(m, 1H), 6.36(dd, 2H, J=3.6, 114.8Hz), 7.37(d, 1H, J=1.7Hz) | 77 | HCl.salt 158–160° C. i-PrOH | 235.0 | n-BuOH K₂CO₃ | 110° C. 9 h B |
| 60 | 173 | 2.00(quint, 2h, J=7.3Hz), 2.75(t, 2H, J=7.6Hz), 3.49–3.64(m, 2H), 3.62(s, 3H), 4.09(t-like, 2H, J=5.6Hz), 4.68(br-s, 1H), 4.79(br-s, 1H), | 58 | maleate | 222.8 | n-BuOH K₂CO₃ | 80° C. 40 h B |

-continued

| Ex. No. | Compound No. | H-NMR data of free base, (CDCl₃) δ (ppm) | Yield of free base (%) | Type of salt M.P. of acid addition salt Recrystallization solvent | UV of acid addition salt EtOH λ max (nm) | Reaction solvent Coexisting base | Reaction temp. Reaction time Reaction vessel |
|---|---|---|---|---|---|---|---|
| | | 5.09(dd, 1H, J=1.3, 10.2Hz), 5.25(dd, 1H, J=1.7, 17.2Hz), 5.93–6.08(m, 2H), 6.28–6.30(m, 1H), 6.35(dd, 2H, J=3.6, 119.8Hz), 7.32(d, 1H), J=1.7Hz) | | | | | |
| 61 | 174 | 3.6(s, 3H), 4.1(t-like, J=6Hz), 4.7(br-s, 1H), 4.8–5.4(m, 5H), 5.8–6.0(m, 1H), 6.3(dd, 2H, J=4, 39Hz), 6.4–7.3(m, 3H) | 78 | HCl.salt | 230.0 | n-BuOH K₂CO₃ | 100° C. 19 h B |
| 62 | 175 | 2.90(t, 2H, J=7.0Hz), 3.63(s,3H), 3.63–3.80(m, 2H), 3.80(s, 3H), 4.12(t-like, 2H, J=5.6Hz), 4.70(br-s, 1H), 4.74(br-s, 1H), 5.10(dd, 1H, J=1.3, 10.2Hz), 5.27(dd, 1H, J=1.7, 17.2Hz), 5.95–6.10(m, 2H), 6.56(d, 1H, J=3.3Hz), 7.00(dd, 4H, J=8.58, 79.2Hz) | 64 | HCl.salt | 228.2 | n-BuOH K₂CO₃ | 100° C. 15 h B |
| 63 | 176 | 1.28(d, 6H, J=6.6Hz), 3.63(s, 3H), 4.10(t-like, 2H, J=5.6Hz), 4.30–4.40(m, 1H), 4.60–4.73(br-s, 2H), 5.09(dd, 1H, J=1.7, 10.2Hz), 5.25(dd, 1H, J=1.7, 17.2Hz), 5.93–6.08(m, 1H), 6.16(d, 1H, J=3.6Hz), 6.57(d, 1H, J=3.3Hz) | 74 | HCl.salt 190–199° C. i-PrOH | 228.6 | n-BuOH K₂CO₃ | 120° C. 15 h A |
| 64 | 177 | 0.98(d, 6H, J=6.6Hz), 1.94(hept, 1H, J=6.6Hz), 3.37(t-like, 2H, J=6.6Hz), 3.63(s, 3H), 4.10(t-like, 2H, J=5.6Hz), 4.69(br-s, 1H), 4.86(br-s, 1H), 5.09(dd, 1H, J=1.7, 10.2Hz), 5.25(dd, 1H, J=1.7, 17.2Hz) 5.93–6.08(m, 1H), 6.17(d, 1H, J=3.6Hz), 6.57(d, 1H, J=3.6Hz) | 65 | HCl.salt 145–148° C. i-PrOH | 229.0 | n-BuOH K₂CO₃ | 120° C. 2.5 h A |
| 65 | 178 | 1.52(s, 9H), 3.61(s, 3H), 4.10(t-like, 2H, J=5.6Hz), 4.60(br-s, 1H), 5.19(dd, 1H, J=1.7, 17.2Hz), 6.04–6.16(m, 1H), 6.09(d, 1H, J=3.3Hz), 6.54(d, 1H, J=3.6Hz) | 4 | HCl.salt | 228.4 | n-BuOH K₂CO₃ | 120° C. 16 h A |
| 66 | 179 | 1.59–1.71(m, 1H), 1.85–2.06(m, 3H), 3.46–3.55(m, 1H), 3.62(s, 3H), 3.76–3.95(m, 3H), 4.07–4.16(m, 3H), 4.71(br-s, 1H), 5.06–5.29(m, 3H), 5.93–6.07(m, 1H), 6.17(d, 1H, J=3.3Hz), 6.56(d, 1H, J=3.6Hz) | 95 | HCl.salt | 228.4 | n-BuOH K₂CO₃ | 120° C. 2.5 h B |
| 67 | 180 | 1.60–1.69(m, 2H), 1.93–2.05(m, 2H), 3.39(d, 3H, J=0.9Hz), 3.45–3.58(m, 3H), 3.63(s, 3H), 4.09(t-like, 2H, J=5.6Hz), 4.23–4.32(m, 2H), 4.65(br-s, 1H), 5.08(dd, 1H, J=1.3, 10.2Hz), 5.25(dd, 1H, J=1.3, 17.2Hz), 5.93–6.07(m, 1H), 6.46(dd, 2H, J=3.6, 76.5Hz) | 29 | HCl.salt | 234.2 | n-BuOH K₂CO₃ | 100° C. 6 h. B |
| 68 | 181 | 1.20(t, 6H, J=6.9Hz), 3.51(q, 4H, J=6.9Hz) 3.62(s, 3H), 3.69(t, 4H, J=6.3Hz), 3.90(t, 4H, J=6.3Hz), 4.06(t-like, 2H, J=6Hz), 4.64(br-s, 1H), 5.07(dd, 1H, J=1.3, 10.2Hz), 5.23(dd, 1H, J=1, 7, 17.2Hz), 5.92–6.06(m, 1H), 6.32(dd, 2H, J=3.6, 79.2Hz) | 59 | HCl.salt | 235.2 | n-BuOH K₂CO₃ | 80° C. 25 h B |
| 69 | 182 | 1.27(3H, d, J=6.9Hz), 1.49–1.85(6H, m), 3.19(1H, dt, J=12.9&2.6Hz), 3.63(3H, s), 4.05–4.16(3H, m), 4.60–4.65(1H, m), 4.98–5.06(1H, m), 5.08(1H, dd, J=10.2&1.3Hz), 5.25(1H, dd, J=17.2&1.7Hz), 5.93–6.07(1H, m), 6.31(1H, d, J=3.6Hz), 6.58(1H, d, J=3.6Hz) | 82 | HCl.salt — EtOH | 299 235 | — K₂CO₃ — | 120° C. 16 h A |
| 70 | 183 | 1.30(6H, d, J=6.9Hz), 1.51–2.04(6H, m), 3.62(3H, s), 4.07(2H, t, J=5.6Hz), 4.77(1H, br), 5.05(1H, br), 5.07(1H, dd, J=10.2&1.0Hz), 5.23(1H, dd, J=17.3&1.2Hz), 5.93–6.07(1H, m), 6.29(1H, d, J=3.6Hz), 6.57(1H, d, J=3.6Hz) | 6 | HCl.salt — | 299 236 | — K₂CO₃ LiI | 160° C. 48 h A |
| 71 | 184 | 3.39(6H, s), 3.49–3.55(2H, m), 3.62–3.67(2H, m), 4.06–4.13(2H, m), 4.51–4.62(1H, m), 4.71–4.76(1H, m), 5.08(1H, dd, J=10.2&1.3Hz), 5.11–5.20(1H, m), 5.24(1H, dd, J=17.1&1.7Hz), 5.92–6.04(1H, m), 6.17(1H, d, J=3.3Hz), 6.57(1H, d, J=3.6Hz) | 23 | HCl.salt — | — | n-BuOH K₂CO₃ — | 120° C. 48 h A |
| 72 | 185 | 1.55–1.75(4H, m), 1.75–2.00(4H, m), 3.33(3H, s), 3.35–3.45(1H, br), 3.61(3H, s), 4.05–4.15(3H, m), 4.65–4.75(2H, br), 5.08(1H, dd, J=10&1Hz), 5.25(1H, dd, J=17&1Hz), 5.93–6.07(1H, m), 6.13(1H, d, J=3.3Hz), 6.56(1H, d, J=3.3Hz) | 35 | HCl.salt — | 296 277 234 | n-BuOH K₂CO₃ LiI | 120° C. 28 h A |
| 73 | 186 | 1.17–1.46(4H, m), 2.08–2.22(4H, m), 3.17(1H, tt, J=10.2&4.0Hz), 3.36(3H, s), 3.62(3H, s), 3.97–4.11(3H, m), 4.63(1H, br), 4.70(1H, t, J=5.94Hz), 5.08(1H, dq, J=10.2&1.3Hz), 5.24(1H, dq, J=17.2&1.7Hz), 5.92–6.07(1H, m), 6.14(1H, d, J=3.3Hz), 6.57(1H, d, J=3.3Hz) | 47 | HCl.salt 202–3° C. CH₃CN | 295 232 | n-BuOH K₂CO₃ LiI | 140° C. 36 h A |
| 74 | 187 | 1.20–1.32(2H, m), 1.22(3H, t, J=6.9Hz), 1.45(2H, dq, J=12.9&3.0Hz), 2.08–2.22(4H, m), | 70 | H₂SO₄.salt 170–2° C. | 293 270 | n-BuOH K₂CO₃ | 120° C. 38 h |

-continued

| Ex. No. | Compound No. | H-NMR data of free base, (CDCl₃) δ (ppm) | Yield of free base (%) | Type of salt M.P. of acid addition salt Recrystallization solvent | UV of acid addition salt EtOH λ max (nm) | Reaction solvent Coexisting base | Reaction temp. Reaction time Reaction vessel |
|---|---|---|---|---|---|---|---|
| | | 3.32(1H, tt, J=10.2&4.0Hz), 3.54(2H, q, J=6.9Hz), 3.58–3.68(4H, m), 3.62(3H, s), 3.95–4.10(3H, m), 4.61–4.72(2H, m), 5.09(1H, dq, J=10.2&1.3Hz), 5.25(1H, dq, 17.2&1.7Hz), 5.93–6.07(1H, m), 6.13(1H, q, J=3.3Hz), 6.57(1H, d, J=3.6Hz) | | CH₃CN | 230 | LiI | A |
| 75 | 188 | 1.53–1.68(2H, m), 2.06–2.11(2H, m), 3.52–3.60(2H, m), 3.65(3H, s), 4.00–4.11(4H, m), 4.29(1H, br), 4.61–4.75(2H, m), 5.12(1H, dd, J=10.2&1.7Hz), 5.27(1H, dd, J=17.2&1.7Hz), 5.91–6.03(1H, m), 6.18(1H, d, J=3.6Hz), 6.62(1H, d, J=3.6Hz) | 30 | HCl.salt — — | 294 232 — | n-BuOH K₂CO₃ — | 160° C. 16 h A |
| 76 | 189 | 1.32–1.47(2H, m), 1.53–1.68(2H, m), 1.84–1.89(2H, m), 2.16–2.21(2H, m), 3.08–3.19(1H, m), 3.14(3H, s), 3.38(3H, s), 3.62(3H, s), 4.05–4.11(2H, m), 4.16–4.73(2H, m), 5.08(1H, dq, J=10.2&1.7Hz), 5.24(1H, dq, J=17.2&1.7Hz), 5.93–6.07(1H, m), 6.33(1H, d, J=3.6Hz), 6.57(1H, d, J=3.3Hz) | 63 | HCl.salt — EtOH | 297 235 | n-BuOH K₂CO₃ LiI | 120° C. 48 h A |
| 77 | 190 | 3.63(3H, s), 3.76(6H, s), 3.90–3.97(2H, m), 4.08–4.17(4H, m), 4.77–4.82(1H, br), 5.10(1H, dd, J=10.2&1.3Hz), 5.11(1H, br), 5.26(1H, dd, J=17.2&1.7Hz), 5.94–6.06(1H, m), 6.09–6.10(1H, m), 6.16–6.17(3H, m), 6.58(1H, d, J=3.6Hz) | 86 | HCl.salt — H₂O | 293 270 228 | n-BuOH K₂CO₃ — | 120° C. 22 h A |

(*A: Autoclave B: Normal pressure and open system)
Wherein, i-PrOH: isopropylalcohol; n-BuOH: N-butylalchol; EtOH: ethylalcohol; (i-Pr)₂O: di-isopropylether Example 78

Effect on Partial Pressure Value of Gases in Arterial Blood (Injection system)

<Method A>

Male Wister strain rats (body weight about 300 g) were anesthetized intra-peritoneally with urethane, and a cannula was inserted into the respiratory tract and the femoral artery, respectively. A suspension (30–100 μm, 10 mg/ml) of carbon powder in a corn oil was intratrachealy injected to induce a hypoxemia state ($PaO_2$; 50–60 mmHg). A compound in accordance with the present invention was continuously intravenously injected into these hypoxemia model animals (0.1 mg/kg/min., 10 min.), and then a partial pressure value of gases ($PaO_2$, $PaCO_2$) in arterial blood was immediately determined.

<Method B>

Male Wister strain rats (body about 300 g) were anesthetized with halothane inhalant, and then 2.0% acetic acid was intratrachealy injected at 0.6 ml/kg to induce a respiratory insufficiency. The animals were intra-peritoneally anesthetized with urethane-α-chloralose, and a cannula was inserted into the femoral artery. After the hypoxemic state ($PaO_2$: 60–70 mmHg) was observed a compound in accordance with the present invention (test substance) was continuously intravenously injected into these hypoxemia model animals (0.1 mg/kg/min., 10 min.), and then a partial pressure value of gases ($PaO_2$, $PaCO_2$) in arterial blood was immediately determined.

The results are as shown in Table 1.

| | | Activity for Increasing $PaO_2$ and Decreasing $PaCO_2$ by Intravenous Injection | |
|---|---|---|---|
| Test Compound | Method | Activity for Increasing $PaO_2$ $\Delta PaO_2$ (mmHg) | Activity for Decreasing $PaCO_2$ $\Delta PaCO_2$ (mmHg) |
| 119 | A | +7.1 | −2.6 |
| 124 | B | +5.7 | −4.0 |
| 133 | A | +6.9 | −0.6 |
| 143 | A | +5.0 | +1.1 |
| 150 | B | +18.4 | −18.6 |
| 156 | B | +19.7 | −9.1 |
| 162 | B | +18.1 | −17.2 |
| 164 | B | +15.4 | −19.2 |
| 165 | B | +7.9 | +1.1 |
| 167 | B | +11.3 | −6.6 |
| 172 | B | +12.3 | −2.8 |
| 173 | B | +12.0 | −13.1 |
| 174 | B | +5.8 | −2.9 |
| 175 | B | +15.2 | −13.1 |
| 176 | B | +22.2 | −14.8 |
| 178 | B | +16.4 | −16.4 |
| 179 | B | +8.5 | +2.4 |
| 180 | B | +6.5 | −0.5 |
| 181 | B | +6.4 | +1.2 |
| 183 | B | +10.7 | −4.6 |
| 184 | B | +7.8 | −0.7 |
| 185 | B | +11.7 | −6.0 |
| 186 | B | +12.3 | −15.4 |
| 187 | B | +13.7 | −14.7 |
| 189 | B | +7.3 | −6.0 |

(Indication of activity)
$\Delta PaO_2$ = ($PaO_2$ after administration − $PaO_2$ before administration) for test compound
$\Delta PaCO_2$ = ($PaCO_2$ after administration − $PaCO_2$ before administration) for test compound

Example 79

Effect on Partial Pressure Value of Gases in Arterial Blood (Oral Administration System)

Method A

Male Wistar strain rats (body weight about 250 g) fasted overnight were anesthetized with halothane inhalant, and a cannula then inserted into the femoral artery. After the animals recovered from the anesthesia, they were again anesthetized with halothane inhalant, and then 2.0% acetic acid was intratrachealy injected at 0.8 ml/kg to induce a hypoxemia state. After the hypoxemic state ($PaO_2$:60–80 mmHg) was observed over about 60 min., a compound in accordance with the present invention (test substance, 10 or 30 mg/kg) was orally administered to the animals. Then 60 min. after the administration, the partial pressure value of gases ($PaO_2$, $PaCO_2$) in arterial blood was determined.

Method B

Male wistar strain rats (body weight about 350 g) were anesthetized with halothane inhalant, and then 2.0% acetic acid were intratrachealy injected at 0.6 ml/kg body to induce a hypoxemia state. In 3 days after injection with 2.0% acetic acid, rats fasted overnight were anesthetized with halothane inhalant, and a cannula inserted into the femoral artery. After these hypoxemia animals ($PaO_2$: 60–80 mmHg) were recovered from the anesthesia, a compound in accordance with the present invention (test substance, 10 or 30 mg/kg) was orally administered to the animals. At 60 min. after the administration, the partial pressure value of gases ($PaO_2$, $PaCO_2$) in arterial blood was determined.

The results are aS shown in Table 2.

Activity for Increasing $PaO_2$ and Decreasing $PaCO_2$ by Oral Administration

| Test Compound | Method | Dose (mg/kg) | Activity for Increasing $PaO_2$ $\Delta PaO_2$ (mmHg) | Activity for Decreasing $PaCO_2$ $\Delta PaCO_2$ (mmHg) |
|---|---|---|---|---|
| 124 | B | 30 | +8.0 | −2.5 |
| 156 | A | 30 | +7.8 | −8.1 |
| 165 | A | 30 | +8.5 | −3.4 |
| 173 | A | 10 | +4.2 | −3.7 |
| 176 | B | 10 | +11.6 | −5.4 |
| 178 | B | 10 | +17.0 | −6.6 |
| 182 | B | 30 | +3.3 | −2.2 |
| 186 | B | 10 | +14.9 | −5.3 |
| 187 | B | 10 | +16.0 | +6.9 |

(Indication of activity)
$\Delta PaO_2$ = ($PaO_2$ after administration − $PaO_2$ before administration) for test compound
$\Delta PaCO_2$ = ($PaCO_2$ after administration − $PaCO_2$ before administration) for test compound

Example 80

Preparation of Tablet

A tablet containing 30 mg of the compound prepared in Example 1 was prepared as follows:

Compound prepared in Ex. 1 30 mg
Lactose 87 mg
Starch 30 mg
Magnesium stearate 3 mg

Example 72

Preparation of Injection

A solution for injection containing 0.3 mg, based on ml of the solution, of the compound prepared in Example 1 was prepared according to the following formulation.

Compound prepared in Ex. 1 30 mg
Sodium chloride 900 mg
Distilled water for injection 100 ml

INDUSTRIAL APPLICABILITY

The compounds in accordance with the present invention, and pharmaceutical preparations thereof, are particularly useful for the treatment of hypoxemia associated with respiratory diseases, and further, an effective process for producing same is provided.

We claim:

1. A pyrrolo[2,3-d]pyrimidine derivative represented by the general formula I:

wherein
$R^1$ represents a hydrogen atom, or an unsubstituted or substituted alkyl, alkenyl or arylalkyl group;

$R^2$ and $R^3$ independently of each other represent a hydrogen atom, or an unsubstituted or substituted alkyl, alkenyl, arylalkyl or alkycarbonyl group; or $R^2$ and $R^3$ are optionally taken together with the adjacent nitrogen atom to form an unsubstituted saturated 5- to 7- member ring, which may be constructed with one or two hereto atoms selected from the group consisting of N, O and S;

$R^4$ and $R^5$ independently of each other represent a hydrogen atom, halogen atom, or an unsubstituted or substituted alkyl group;

Y is a linking group bonded to the pyrimidine ring via a nitrogen atom therein of the formula:

wherein G represents a hydrogen atom or an alkyl group;

Z represents a group bonded to a carbon or nitrogen atom in the linking group, and is a hydrogen atom, an unsubstituted or substituted alkyl, alkenyl, aryl, heteroaryl, arylalkyl, heteroarylalkyl, alkylcarbonyl, arylcarbonyl, heteroarylcarbonyl, arylalkylcarbonyl, heteroarylalkylcarbonyl, alkyloxycarbonyl, alkylcarbonyloxy, arylcarbonyloxy, arylalkylcarbonyloxy, heteroarylalkylcarbonyloxy, alkyloxy or alkyloxyimino-alkyl group; or mono- or di-alkylamino, mono- or di-alkylcarbonylamino or N-alkyl-N-alkylcarbonylamino group; or represents a group bonded to a carbon atom in the linking group, and is a carboxyl or hydroxyl group; or Y and Z are taken together to form morpholino or thiomorpholino group;

each substituent in said substituted group is substituted at a chain or cyclic moiety of the alkyl, alkenyl, arylalkyl, heteroarylalkyl, aryl, or heteroaryl moiety, respectively, and represents an alkyl, alkyloxy, alkylcarbonyl, alkylcarbonyloxy, hydroxy, mono- or di-alkylamino, amino, nitro, cyano group, or a halogen atom, wherein the heteroaryl groups represent respectively a group selected from the group consisting of pyrrolyl, furyl, thienyl, and pyridyl, with a proviso that $R^2$ and $R^3$ do not represent a hydrogen atom at the same time, and that when $R^1$ represents a hydrogen atom, the combinations wherein one of $R^2$ and $R^3$ represents a hydrogen atom and another represents an alkyl group are excluded; or a pharmaceutically acceptable acid addition salt thereof.

2. A pyrrolo[2,3-d]pyrimidine derivative or a pharmaceutically acceptable acid addition salt thereof in accordance with claim 1, wherein $R^1$, $R^2$, $R^3$, $R^4$, $R^5$, Y and Z are as defined above, with a proviso that $R^2$ and $R^3$ do not represent a hydrogen atom at the same time, and that when $R^1$ represents a hydrogen atom, the combinations wherein one of $R^2$ and $R^3$ represents a hydrogen atom and another represents an alkyl group are excluded, and that when Y is —N(G)—, G represents a hydrogen atom, the case wherein Z represents a hydrogen atom is excluded.

3. A pyrrolo[2,3-d]pyrimidine derivative or a pharmaceutically acceptable acid addition salt thereof in accordance with claim 1, wherein $R^1$, $R^2$, $R^3$, $R^4$, $R^5$, Y and Z are as defined above, with a proviso that $R^2$ and $R^3$ do not represent a hydrogen atom at the same time, and that when $R^1$ represents a hydrogen atom, the combinations wherein one of $R^2$ and $R^3$ represents a hydrogen atom and another represents an alkyl group are excluded, and that when Y is linking group —N(G)—, the case wherein $R^1$ represents an arylalkyl is excluded.

4. A pyrrolo[2,3-d]primidine derivative or a pharmaceutically acceptable acid addition salt thereof in accordance with claim 1, wherein Y is a linking group having the formula:

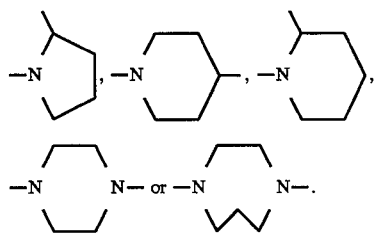

5. A pyrrolo[2,3-d]pyrimidine derivative or a pharmaceutically acceptable acid addition salt thereof in accordance with claim 1, wherein Y is a group —N(G)—, and G is a hydrogen atom, methyl group or ethyl group.

6. A pyrrolo[2,3-d]pyrimidine derivative or a pharmaceutically acceptable acid addition salt thereof in accordance with claim 1, wherein $R^1$ is a lower alkyl group or allyl group.

7. A pyrrolo[2,3-d]pyrimidine derivative or a pharmaceutically acceptable acid addition salt thereof in accordance with claim 1, wherein $R^2$ is a hydrogen atom, $R^3$ is an alkyl group, allyl group or 2-methylallyl group.

8. A pyrrolo[2,3-d]pyrimidine derivative or a pharmaceutically acceptable acid addition salt thereof in accordance with claim 1, wherein $R^4$ and $R^5$ are a hydrogen atom.

9. A pyrrolo[2,3-d]pyrimidine derivative or a pharmaceutically acceptable acid addition salt thereof in accordance with claim 1, wherein $R^1$ is methyl group or allyl group; $R^2$ is a hydrogen atom; $R^3$ is cyclopropylmethyl group;]allyl group or 2-methylallyl group; $R^4$ and $R^5$ are a hydrogen atom; Y is a linking group having the formula:

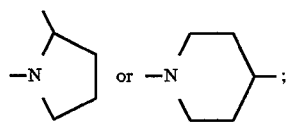

and Z is a hydrogen atom, alkyl group, alkylcarbonyl group, alkyloxycarbonyl group or alkylcarbonyloxy group; or Y is a linking group having the formula:

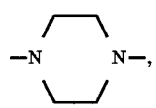

and Z is an alkyl group, or an unsubstituted or substituted arylalkyl group; or Y is a linking group having the formula: —N(G)—, G is a hydrogen atom or alkyl group, and Z is an allyl group, arylalkyl group, or heteroarylalkyl group which may be substituted by one to three methyl groups on the alkyl chain; or Y and Z taken together is a morpholino group.

10. A pyrrolo[2,3-d]pyrimidine derivative or a pharmaceutically acceptable acid addition salt thereof in accordance with claim 1, wherein $R^1$ is a methyl group or allyl group; $R^2$ is a hydrogen atom; $R^3$ is a cyclopropyl-methyl group, allyl group or 2-methylallyl group; Y is a linking group having the formula:

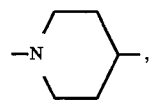

and Z is a hydrogen atom; or Y is a linking group having the formula:

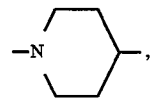

and Z is a hydrogen atom, isopropyloxycarbonyl group or acetyloxy group; or Y is a linking group having the formula:

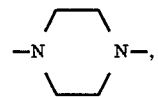

and Z is a methyl group or bis(4-fluorophenyl)methyl group; or Y is a linking group having the formula: —NH—, and Z is an allyl group, benzyl group, 1-phenylethyl group, 1-methyl-1-phenylethyl group, 2-phenylethyl group, 1-(1-naphthyl)ethyl group, 1,2,3,4-tetrahydronaphthalene-1-yl group, furfuryl group, 3-(2-furyl)propyl group or 2-thienylmethyl group; or Y is a linking group having the formula:

—N(CH₃)—, and Z is methyl group, benzyl group or phenethyl group.

11. A method for treating hypoxemia comprising administering an effective amount of a pyrrolo[2,3-d]pyrimidine derivative or a pharmaceutically acceptable acid addition salt thereof in accordance with claim 1.

12. A pharmaceutical preparation for therapy of hypoxemia, comprising an effective amount of a pyrrolo[2,3-d]pyrimidine derivative or a pharmaceutically acceptable acid addition salt thereof in accordance with claim 1.

* * * * *